(12) United States Patent
Henning et al.

(10) Patent No.: US 11,071,982 B2
(45) Date of Patent: Jul. 27, 2021

(54) FLUID HOLDING AND DISPENSING MICRO-FEATURE

(71) Applicant: ATIVA MEDICAL CORPORATION, St. Paul, MI (US)

(72) Inventors: Phillip Henning, Minneapolis, MN (US); Elizabeth Palaima, St. Paul, MN (US); Pamela Wong, St. Paul, MN (US); Daniel R. McPeak, Minneapolis, MN (US); Ka Man Lee, Minneapolis, MN (US); Eric R. Peltola, Minneapolis, MN (US)

(73) Assignee: Ativa Medical Corporation, St. Paul, MN (US)

(*) Notice: Subject to any disclaimer, the term of this patent is extended or adjusted under 35 U.S.C. 154(b) by 698 days.

(21) Appl. No.: 15/755,676

(22) PCT Filed: Aug. 29, 2016

(86) PCT No.: PCT/US2016/049324
§ 371 (c)(1),
(2) Date: Feb. 27, 2018

(87) PCT Pub. No.: WO2017/035539
PCT Pub. Date: Mar. 2, 2017

(65) Prior Publication Data
US 2019/0022651 A1    Jan. 24, 2019

Related U.S. Application Data

(63) Continuation-in-part of application No. 14/837,524, filed on Aug. 27, 2015, now abandoned.

(51) Int. Cl.
*G01N 1/40* (2006.01)
*G01N 33/80* (2006.01)
(Continued)

(52) U.S. Cl.
CPC ... *B01L 3/502753* (2013.01); *B01L 3/502707* (2013.01); *C12Q 1/24* (2013.01);
(Continued)

(58) Field of Classification Search
None
See application file for complete search history.

(56) References Cited

U.S. PATENT DOCUMENTS

| 3,521,715 A | 7/1970 | Krutein |
| 4,038,875 A | 8/1977 | Walkotten |

(Continued)

FOREIGN PATENT DOCUMENTS

| CN | 101939645 | 1/2011 |
| CN | 102918162 | 2/2013 |

(Continued)

OTHER PUBLICATIONS

Haandel and van der Lubbe, "Handbook Biological Waste Water Treatment: Design and optimisation of activated sludge systems," Chapt. 6, pp. 248-255, 2007.

(Continued)

*Primary Examiner* — Brian R Gordon
(74) *Attorney, Agent, or Firm* — Fish & Richardson P.C.

(57) ABSTRACT

Apparatus, system and method for dispensing a particle-laden fluid from a fluid holding and dispensing micro-feature and/or multiple lysing channel structures. In some implementations, the apparatus includes: a chamber having one or more surfaces that define a volume to receive fluid containing particulate matter, a soluble surface coating on a portion of the one or more surfaces of the chamber, and an outlet port to dispense at least a portion of the fluid from the chamber. In some implementations, the particle-laden fluid may be whole blood, and the soluble surface coating may include reagents and/or dyes that are diffused into the whole (Continued)

blood received within the chamber to generate signals to visualize various cellular components. In some implementations, the apparatus may also include a second soluble surface coating on portions of surfaces of the multiple lysing channel structures.

16 Claims, 12 Drawing Sheets

(51) Int. Cl.
*B01L 3/00* (2006.01)
*C12Q 1/24* (2006.01)
*G01N 15/06* (2006.01)
*G01N 15/04* (2006.01)
*G01N 15/00* (2006.01)
*G01N 15/14* (2006.01)

(52) U.S. Cl.
CPC ........... *G01N 1/4077* (2013.01); *G01N 15/06* (2013.01); *G01N 33/80* (2013.01); *B01L 2200/0652* (2013.01); *B01L 2200/10* (2013.01); *B01L 2300/0816* (2013.01); *B01L 2300/0858* (2013.01); *B01L 2300/0864* (2013.01); *B01L 2300/0887* (2013.01); *B01L 2300/16* (2013.01); *B01L 2400/0457* (2013.01); *G01N 15/04* (2013.01); *G01N 2015/0053* (2013.01); *G01N 2015/0693* (2013.01); *G01N 2015/1486* (2013.01)

(56) References Cited

U.S. PATENT DOCUMENTS

| | | | |
|---|---|---|---|
| 4,040,959 A | | 8/1977 | Irwin et al. |
| 5,726,026 A * | | 3/1998 | Wilding ............. B01D 67/0062 366/DIG. 3 |
| 5,945,070 A * | | 8/1999 | Kath .................... B01J 19/0046 422/535 |
| 6,136,272 A | | 10/2000 | Weigl |
| 6,159,739 A | | 12/2000 | Weigl |
| 6,186,409 B1 | | 2/2001 | Srinath et al. |
| 6,382,228 B1 | | 5/2002 | Cabuz et al. |
| 6,454,945 B1 | | 9/2002 | Weigl |
| 6,488,894 B1 | | 12/2002 | Miethe |
| 6,537,501 B1 | | 3/2003 | Holl et al. |
| 6,541,213 B1 | | 4/2003 | Weigl |
| 6,549,275 B1 | | 4/2003 | Cabuz et al. |
| 6,557,427 B2 | | 5/2003 | Weigl et al. |
| 6,674,525 B2 | | 1/2004 | Bardell et al. |
| 6,706,245 B2 | | 3/2004 | Neal |
| 7,061,595 B2 | | 6/2006 | Cabuz et al. |
| 7,229,594 B2 | | 6/2007 | Renaud |
| 7,242,474 B2 | | 7/2007 | Cox et al. |
| 7,277,166 B2 | | 10/2007 | Padmanabhan et al. |
| 7,420,659 B1 | | 9/2008 | Cabuz et al. |
| 7,517,498 B2 | | 4/2009 | Fredrick |
| 7,527,109 B2 | | 5/2009 | Barker |
| 7,550,267 B2 * | | 6/2009 | Hawkins .......... G01N 33/54366 422/504 |
| 7,641,856 B2 | | 1/2010 | Padmanabhan et al. |
| 7,790,115 B2 * | | 9/2010 | Sogaro ................... B01L 3/502 422/400 |
| 7,988,935 B2 * | | 8/2011 | Yuan ....................... B01L 3/502 422/527 |
| 8,034,296 B2 | | 10/2011 | Cox et al. |
| 8,071,051 B2 | | 12/2011 | Padmanabhan et al. |
| 8,097,225 B2 | | 1/2012 | Padmanabhan et al. |
| 8,323,564 B2 | | 12/2012 | Padmanabhan et al. |
| 8,329,118 B2 | | 12/2012 | Padmanabhan et al. |
| 8,361,410 B2 | | 1/2013 | Padmanabhan et al. |
| 8,372,354 B2 | | 2/2013 | Killen |
| 8,383,043 B2 | | 2/2013 | Padmanabhan et al. |
| 8,741,233 B2 | | 6/2014 | Bardell et al. |
| 9,366,606 B1 * | | 6/2016 | McPeak .................. G01N 1/38 |
| 2002/0037499 A1 * | | 3/2002 | Quake ....................... B01L 3/02 435/6.13 |
| 2002/0042125 A1 * | | 4/2002 | Petersen ............ G01N 30/6095 435/287.2 |
| 2002/0123154 A1 * | | 9/2002 | Burshteyn ............ B01D 61/147 436/177 |
| 2004/0043506 A1 | | 3/2004 | Haussecker et al. |
| 2006/0073075 A1 * | | 4/2006 | Nagaoka .......... G01N 35/00029 422/64 |
| 2006/0246575 A1 | | 11/2006 | Lancaster et al. |
| 2006/0263888 A1 | | 11/2006 | Fritz et al. |
| 2008/0153152 A1 * | | 6/2008 | Wakabayashi ...... B01F 13/1013 435/287.2 |
| 2009/0101575 A1 * | | 4/2009 | Alburty ..................... C12Q 1/24 210/636 |
| 2010/0035245 A1 * | | 2/2010 | Stiene ............... B01L 3/502707 435/6.12 |
| 2010/0104479 A1 | | 4/2010 | Alex et al. |
| 2011/0275111 A1 | | 11/2011 | Pettigrew et al. |
| 2013/0095007 A1 | | 4/2013 | Haubert |
| 2013/0203157 A1 | | 8/2013 | Cheung et al. |
| 2014/0008210 A1 | | 1/2014 | Antonio et al. |
| 2014/0234828 A1 | | 8/2014 | Walter |
| 2014/0315238 A1 | | 10/2014 | Farrell et al. |
| 2015/0165346 A1 | | 6/2015 | Michael et al. |
| 2015/0226657 A1 * | | 8/2015 | Foster .................... G01N 15/10 435/287.1 |
| 2017/0059590 A1 | | 3/2017 | McPeak et al. |
| 2017/0074759 A1 | | 3/2017 | Campton |
| 2017/0114386 A1 | | 4/2017 | McPeak et al. |

FOREIGN PATENT DOCUMENTS

| | | |
|---|---|---|
| WO | WO 1999025475 | 5/1999 |
| WO | WO 2007076549 | 7/2007 |
| WO | WO 2014145330 | 9/2014 |
| WO | WO 2014149310 | 9/2014 |
| WO | WO 2015009284 | 1/2015 |

OTHER PUBLICATIONS

International Preliminary Report on Patentability in Internation Application No. PCT/US2016/049324.
International Search Report and Written Opinion for International Application No. PCT/US2016/049324, dated Nov. 24, 2016, 11 pages.
Szeto et al., "Microfluidic squeezing for intracellular antigen loading in polyclonal B-cells as cellular vaccines," *Sci Rep.* 5:10276, 13 pages, May 22, 2015.
Yflow, "Coaxial Electrospinning Machines: R&D Microencapsulation," [retrieved Sep. 11, 2015]. Retrieved from the Internet: <URL:http://www.yflow.com/technology/coaxial_coflowing/>, 4 pages.
Chinese Office Action in Application No. 201680057400, dated Mar. 17, 2020, 20 pages.
"Proceedings of the Sixth World Petroleum Conference, the second volume Drilling and Production Operations, the second fascicle, drilling part", pp. 57-58, 1965, English Abstract.
Zhengyao Li et al., "Mineral chemical treatment", pp. 61-31, 2015, English Abstract.

* cited by examiner

FLUID HOLDING AND DISPENSING MICRO-FEATURE

RELATED APPLICATIONS

This application is a National Stage Application under 35 U.S.C. § 371 and claims the benefit of International Application No. PCT/US2016/049324, filed Aug. 29, 2016, which is a continuation-in-part of and claims priority under 35 U.S.C. § 120 to U.S. patent application Ser. No. 14/837,524, now abandoned, titled "FLUID HOLDING AND DISPENSING MICRO-FEATURE," which was filed on Aug. 27, 2015, the entire contents of each of which are hereby incorporated herein by reference for all purposes.

TECHNICAL FIELD

The present specification relates to fluid dispensing features for use with fluidic devices, such as microfluidic devices that perform cell counting techniques.

BACKGROUND

When dispensing fluids containing particulate matter, such as whole blood containing blood cells (example particulate matter), sedimentation can occur over time as the particulate matter settles out. Such sedimentation can result in regions of the fluid becoming inhomogeneous with different concentrations of the particulate matter. Techniques to agitate fluids with particulate matter have been used to avoid the effects of sedimentation and to ensure that fluids are dispensed with the same or similar concentrations of particulate matter. A variety of agitation techniques have been used, such as shaking a container holding a fluid with particulate matter and mixing/stirring such a fluid within a container.

Fluid dispensing techniques have been used in a variety of applications, such as cell counting techniques that allow for quantification of particulate matter within liquid media, such as blood, plasma, or lymph. In clinical practice, cell counting has been used to provide information related to physiological conditions that indicate, or result from, the presence of infectious diseases. For example, complete blood count (CBC) can be used for medical diagnosis and treatment of various diseases.

SUMMARY

This document generally describes fluid holding and dispensing micro-features that can be used to dispense fluids containing particulate matter over time with near uniform concentrations of particulate matter without using techniques to agitate the fluid and to avoid the effects of sedimentation. Such fluid holding and dispensing micro-features can allow for the measurement of particulate concentration within a particle-laden fluid based on the volumetric displacement of the fluid through the micro-feature.

For example, such a micro-feature can include a chamber that is oriented perpendicular to an outlet port such that the particle transport rate out of the chamber is proportional to the volumetric flow rate of a particle-laden fluid from the chamber and the proportionality constant represents the particulate concentration within the fluid. The outlet port can be positioned on a vertical sidewall of the chamber such that the fluid exiting the chamber additionally follows a constant particle flow rate that is in agreement with the concentration of the particulate matter within the fluid. Accordingly, the micro-feature can be used to inferentially determine the particulate concentration of the fluid within the chamber based on measuring the bulk volumetric flow rate of dispensed fluid through the outlet port.

In another example, a micro-feature can also include multiple lysing channel structures that are coupled to each other to pass a fluid sample in sequence between the lysing channel structures and then to a test chamber. The multiple lysing channel structures can be shaped as an "F" and placed on alternate layers of a multiple layer cartridge. The arrangement of the multiple lysing channel structures can be coupled to form a chaotic advection micromixer to aid in cell lysis. Upon exiting the last lysing channel structure, the fluid sample is sufficiently lysed and is provided to a measuring chamber such as a cuvette for analysis.

The surfaces of the micro-features may be deposited with fluids containing soluble substances. In some instances, the deposited fluid may be evaporated onto the surfaces to create dried soluble substance coatings onto the surfaces of the micro-features. In this regard, the micro-features may be used to mix portions of the sample fluids received by the micro-features and the soluble substances to enable the use of the micro-features as room temperature assays within a disposable cartridge. The assays may include the use of compounds that are stable at room temperature, or the use of compounds that require refrigeration (e.g., antibodies) but are lyophilized onto the surfaces of the micro-features in order to enable use at room temperature. In some instances, a single cartridge may include multiple micro-features with different soluble substance coatings to allow the performance of multiple assays on a cartridge using one sample fluid.

Implementations may include one or more of the following features. For example, an apparatus for dispensing fluid, the apparatus including: a chamber having one or more surfaces that define a volume to receive fluid containing particulate matter, where the fluid within the chamber includes, at least, a top region, a middle region, and a bottom region that, after at least a threshold time period has elapsed since the fluid is received into the chamber, contain different concentrations of the particulate matter, with (i) the top region containing less than or equal to a first threshold concentration of the particulate matter, (ii) the middle region containing between the first threshold concentration of the particulate matter and a second threshold concentration of the particulate matter, and (iii) the bottom region containing greater than or equal to the second threshold concentration of the particulate matter, where the first threshold concentration is less than the second threshold concentration; and an outlet port to dispense at least a portion of the fluid from the chamber in concentrations that are between the first threshold concentration and the second concentration, the outlet port (i) located at a position in the chamber that corresponds to the middle region and (ii) having a normal vector that, when the apparatus is positioned to dispense the fluid, is substantially perpendicular to gravity.

One or more implementations of the apparatus may include the following optional features. For example, in some implementations, the fluid containing particulate matter includes whole blood (or whole blood components) and the particulate matter includes blood cells.

In some implementations, after at least the threshold time period has elapsed since the whole blood is received into the chamber, the: the top region contains a plasma supernatant of the whole blood; the middle region contains pristine blood with blood cell concentrations that are within a threshold range of a blood cell concentration of the whole blood when it is initially received into the chamber; and the bottom layer contains a packed cell layer that results from sedimentation over the threshold time period.

In some implementations, the apparatus further includes one or more inlet ports for the chamber that are configured to receive another fluid that, once received into the chamber, will force the fluid in the middle region of the chamber to be dispensed through the outlet port in the direction that is substantially perpendicular to gravity.

In some implementations, at least one of the one or more inlet ports is connected to the top region of the chamber, and the other fluid received through the at least one of the one or more inlet ports is less dense than the fluid containing particulate matter.

In some implementations, at least one of the one or more inlet ports is connected to bottom region of the chamber, and the other fluid received through the at least one of the one or more inlet ports is more dense than the fluid containing particulate matter.

In some implementations, the one or more inlet ports include, at least, (i) a first inlet port that is connected to the top region of the chamber and (ii) a second inlet port that is connected to the bottom region of the chamber, the other fluid includes a first fluid received through the first inlet port that is less dense than the fluid containing particulate matter, and the other fluid additionally includes a second fluid received through the second inlet port that is more dense than the fluid containing particulate matter.

In some implementations, the middle region decreases in size and the top and bottom regions increase in size over time as sedimentation of the particulate matter in the fluid occurs.

In some implementations, the outlet port is positioned along at least one vertical sidewall of the chamber on a plane that corresponds to an average point of convergence between the top region and the bottom region across a range of fluid samples containing the particulate matter.

In some implementations, the apparatus further includes an microfluidic cartridge that includes one or more microfluidic circuits through which the fluid dispensed from the chamber via the outlet port is analyzed, and the microfluidic cartridge is configured to be inserted into an analyzer device that is configured and programmed to (i) control the fluid being dispensed from the chamber and (ii) analyze the fluid dispensed from the chamber.

In some implementations, the microfluidic cartridge is disposable.

In some implementations, the apparatus further includes an analyzer device that is configured and programmed to (i) control the fluid being dispensed from the chamber and (ii) analyze the fluid dispensed from the chamber.

In some implementations, the apparatus further includes a second outlet port to dispense at least a portion of the fluid from the chamber in concentrations that are between the first threshold concentration and the second concentration, the second outlet port (i) located at a position in the chamber that corresponds to the middle region and (ii) having a normal vector that, when the apparatus is positioned to dispense the fluid, is substantially perpendicular to gravity.

In some implementations, a method may include: injecting a fluid containing particulate matter into a fluidic circuit including at least (i) a chamber having one or more surfaces that define a volume to receive the fluid containing particulate matter, where the fluid within the chamber includes, at least, a top region, a middle region, and a bottom region that, after at least a threshold time period has elapsed since the fluid is received into the chamber, contain different concentrations of the particulate matter, and (ii) an outlet port located at a position in the chamber that corresponds to the middle region; dispensing a portion of the fluid containing particulate matter from the middle region of the chamber via the outlet port such that the fluid containing particulate matter flows from the chamber and into the outlet port in a direction that is substantially perpendicular to gravity; and stopping, while the top and bottom regions of the chamber still include another portion of the fluid containing particulate matter, the dispensing of the fluid containing particulate matter based on one or more criteria being met.

One or more implementations of the method may include the following optional features. For example, in some implementations, the one or more criteria being met include a particular period of time having elapsed since the fluid containing particulate matter was injected into the fluidic circuit having elapsed, and the particular period of time corresponds to the fluidic circuit.

In some implementations, the method further includes: measuring, by an analyzer device, a number of individual particles from the fluid that flow through the outlet port over a period of time; measuring, by the analyzer device, a total volume of the fluid dispensed through the outlet port over the period of time; calculating, by the analyzer device, a remaining concentration of the particulate matter within the chamber based at least on (i) the number of individual particles measured as flowing through the outlet port, and (ii) the measured total volume of the fluid dispensed over the period of time; and determining, by the analyzer device, whether the remaining concentration of the particulate matter in the fluid is greater than a threshold concentration for dispensing through the outlet port, where the one or more criteria being met include the remaining concentration of the particulate matter being greater than the threshold concentration.

In some implementations, the fluid containing particulate matter includes whole blood, and determining the remaining concentration of the particulate matter within chamber includes determining a red blood cell concentration within the whole blood in the chamber.

In some implementations, the number of individual particles is measured for fluid contained in the middle region of the fluid in the chamber having a threshold concentration of the particulate matter that is (i) greater than a first threshold concentration of the particulate matter within the top region of the chamber, and (ii) less than a second threshold concentration of the particulate matter within the bottom region.

In some implementations, the number of individual particles is measured using one or more optical detectors that are part of or in communication with the analyzer device.

In some implementations, the dispensing includes injecting another fluid into the chamber after injecting the fluid containing particulate matter into the fluidic circuit, where the other fluid forces individual particles from among the particulate matter of the fluid to be dispensed through the outlet port.

In some implementations, injecting the another fluid into the chamber includes injecting the other fluid into at least one of one or more inlet ports that is connected to the top region of the chamber, where the other fluid is less dense than the fluid containing particulate matter.

In some implementations, injecting the reagent fluid into the chamber includes injecting the other fluid into at least one of one or more inlet ports that is connected to the bottom region of the chamber, where the other fluid is more dense than the fluid containing particulate matter.

In some implementations, the fluid containing particulate matter includes whole blood, and after at least the threshold time period has elapsed since the whole blood is received into the chamber: the top region contains a plasma supernatant of the whole blood, the middle region contains pristine blood with blood cell concentrations that are within a threshold range of a blood cell concentration of the whole blood when it is initially received into the chamber, and the bottom layer contains a packed cell layer that results from sedimentation over the threshold time period.

In some implementations, the method further includes dispensing a portion of the fluid containing particulate matter from the middle region of the chamber via a second outlet port such that the fluid containing particulate matter flows from the chamber and into the outlet port in a direction that is substantially perpendicular to gravity.

In some implementations, a system for dispensing fluid includes: a fluidic circuit configured to receive a fluid containing particulate matter; a chamber having one or more surfaces that define a volume to receive the fluid containing particulate matter from the fluidic circuit, where the fluid within the chamber includes, at least, a top region, a middle region, and a bottom region that, after at least a threshold time period has elapsed since the fluid is received into the chamber, contain different concentrations of the particulate matter, with (i) the top region containing less than or equal to a first threshold concentration of the particulate matter, (ii) the middle region containing between the first threshold concentration of the particulate matter and a second threshold concentration of the particulate matter, and (iii) the bottom region containing greater than or equal to the second threshold concentration of the particulate matter, where the first threshold concentration is less than the second threshold concentration; and a outlet port, positioned along at least one vertical wall of the chamber, configured to receive a portion of the fluid from the chamber in concentrations that are between the first threshold concentration and the second concentration, the outlet port (i) located at a position in the chamber that corresponds to the middle region and (ii) having a normal vector that, when the apparatus is positioned to dispense the fluid, is substantially perpendicular to gravity.

In some implementations, the system further includes an analyzer device that is configured and programmed to (i) control the fluid being dispensed from the chamber and (ii) analyze the fluid dispensed from the chamber.

In some implementations, the analyzer device includes the fluidic circuit, the chamber, and the outlet port.

In some implementations, the system further includes a cartridge that is configured to be inserted into the analyzer device, where the cartridge includes the fluidic circuit, the chamber, and the outlet port.

In some implementations, the system further includes a second outlet port, positioned along at least one vertical wall of the chamber, configured to receive a portion of the fluid from the chamber in concentrations that are between the first threshold concentration and the second concentration, the second outlet port (i) located at a position in the chamber that corresponds to the middle region and (ii) having a normal vector that, when the apparatus is positioned to dispense the fluid, is substantially perpendicular to gravity.

In another implementation, an apparatus includes a chamber having one or more surfaces that define a volume to receive fluid containing particulate matter, wherein the chamber includes, at least, a top region, a middle region, and a bottom region that, after at least a threshold time period has elapsed since the fluid is received into the chamber, contain different concentrations of the particulate matter, with (i) the top region containing less than or equal to a first threshold concentration of the particulate matter, (ii) the middle region containing between the first threshold concentration of the particulate matter and a second threshold concentration of the particulate matter, and (iii) the bottom region containing greater than or equal to the second threshold concentration of the particulate matter, wherein the first threshold concentration is less than the second threshold concentration. A first soluble substance coating can be included on at least a portion of the one or more surfaces of the chamber that, after the fluid is received into the chamber, diffuses into at least a portion of the fluid received into the chamber, wherein the first soluble substance coating includes a particular concentration of a compound that diffuses with the particulate matter. An outlet port can also be included to dispense at least a portion of the fluid from the chamber in concentrations that are between the first threshold concentration and the second concentration, the outlet port is located at a position in the chamber that corresponds to the middle region.

Certain implementations can optionally include one or more of the following features. The first soluble substance coating can include a fluorescent dye, and at least a portion of the particular matter dispensed from the outlet port is tagged with the fluorescent dye. The fluid containing particulate matter can be whole blood. The fluorescent dye can be a Neutral red dye. The particular concentration of the Neutral red dye within the first soluble substance coating can be sufficient to fluorescently tag eosinophils within the portion of the whole blood that is dispensed from the outlet port. The first soluble substance coating can be a hydrophilic coating. The first soluble substance coating can be a sample modifier that reacts with the particulate matter. The sample modifier can be an antibody. The first soluble substance coating can be a dried reagent and a carrier fluid, wherein the carrier fluid evaporates from at least a portion of the one or more surfaces of the chamber before the fluid is received into the chamber. The first soluble substance coating can be on an entirety of each of the one of more surfaces is coated with the first soluble substance. The first soluble substance coating can be on portions of three of the one or more surfaces that does not include the outlet port. The portions of the three of the one or more surfaces can coincide with the middle region containing between the first threshold concentration of the particulate matter and the second threshold concentration of the particulate matter. The apparatus can further include multiple lysing channel structures coupled to each other to pass the fluid containing particulate matter in sequence between the lysing channel structures; a second soluble substance coating on at least a portion of the surfaces of the multiple lysing channel structures that, after the fluid is received into the multiple lysing channel structures, diffuses into a portion of the fluid received into the multiple lysing channel structures; and a test chamber to receive the fluid containing particulate matter from the multiple lysing channel structures. The first soluble substance coating and the second soluble substance coating can each include different soluble substances. The fluid that is received into the chamber and the fluid that is received into the multiple lysing channel structures can be different portions of the same fluid sample. The fluid containing particulate matter can be whole blood. The second soluble substance coating can include sodium deoxycholate and at least one additive that, after the second soluble substance diffuses into the portion of the whole blood received into the multiple lysing channel structures, prevents an increase in viscosity of the portion of whole blood received into the multiple lysing channel structures. Each of the multiple lysing channel structures can include a substantially straight backbone channel having a base portion; and a top portion with two equal lengths, substantially parallel side channels extending substantially orthogonal to the top portion of the backbone channel. The multiple lysing channel structures can be arranged such that a first lysing channel structure receives the fluid containing particulate matter at the base portion, and a second lysing channel structure has an end of the base portion coupled to receive the fluid containing particulate matter from the top portion with two equal lengths.

In another implementation, a method includes depositing a first liquid with a first soluble substance onto a portion of one or more surfaces of a chamber of a fluidic circuit comprising: (i) chamber having one or more surfaces that define a volume to receive the fluid containing particulate matter, wherein the chamber includes, at least, a top region, a middle region, and a bottom region that, after at least a threshold time period has elapsed since the fluid is received into the chamber, contain different concentrations of the particulate matter, and (ii) an outlet port located at a position in the chamber that corresponds to the middle region; injecting a fluid containing particulate matter into the fluidic circuit; diffusing a portion of the first soluble substance deposited onto the portion of one or more surfaces of the chamber into at least a portion of the injected fluid containing particulate matter; dispensing a portion of the fluid containing particulate matter from the middle region of the chamber via the outlet port such that (i) the fluid containing particulate matter flows from the chamber and into the outlet port in a direction that is substantially perpendicular to gravity, and (ii) the portion of the fluid dispensed via the outlet port has been diffused into at least a portion of the first soluble substance.

Certain implementations can optionally include one or more of the following features. The first soluble substance coating can be a fluorescent dye, and the portion of the fluid dispensed from the chamber can be tagged with the fluorescent dye. The fluid containing particulate matter can be whole blood, the fluorescent dye cam be a Neutral red dye, and the concentration of the Neutral red dye within the first soluble substance coating can be sufficient to fluorescently tag eosinophils within the portion of the whole blood that is dispensed from the outlet port. The first soluble substance coating can be a hydrophilic coating. The first soluble substance coating can be a dried reagent and a carrier fluid, wherein the carrier fluid evaporates from the at least a portion of the one or more surfaces of the chamber before the fluid is received into the chamber. The first soluble substance coating can be on an entirety of each of the one of more surfaces is coated with the first soluble substance. The first soluble substance coating can be on portions of three of the one or more surfaces that does not include the outlet port. The portions of the three of the one or more surfaces can coincide with the middle region containing between the first threshold concentration of the particulate matter and the second threshold concentration of the particulate matter. The method can further include depositing a second liquid with a second soluble substance onto a portion of one or more surfaces of multiple lysing channel structures of the fluidic circuit, wherein the multiple lysing channel structures are coupled to each other to pass the fluid containing particulate matter in sequence between the lysing channel structures; diffusing a portion of the second soluble substance deposited onto the portion of one or more surfaces of the multiple lysing channel structures into at least a portion of the injected fluid containing particulate matter and; and dispensing a portion of the fluid containing particular matter from the multiple lysing channel structures such that the portion of the fluid dispensed via the multiple lysing channel structures having been diffused into at least a portion of the second soluble substance. The first soluble substance and the second soluble substance can each include different soluble substances. The portion of the injected fluid containing particulate matter that is diffused into the portion of the soluble substance can be deposited onto the portion of the one or more surfaces of the chamber and the portion of the injected fluid containing particulate matter that is diffused into the portion of the second soluble substance deposited onto the portion of the one or more surfaces of the multiple lysing channel structures are different portions of the same injected fluid. Fluid containing particulate matter can be whole blood, and the second soluble substance coating can include sodium deoxycholate and at least one additive that, after the soluble substance diffuses into the portion of the whole blood received into the multiple lysing channel structures, prevent an increase in viscosity of the portion of whole blood received into the multiple lysing channel structures. Each of the multiple lysing channel structures can include a substantially straight backbone channel having a base portion; and a top portion with two equal lengths, substantially parallel side channels extending substantially orthogonal to the top portion of the backbone channel. The multiple lysing channel structures can be arranged such that: a first lysing channel structure receives the fluid containing particulate matter at the base portion, and a second lysing channel structure has an end of the base portion coupled to receive the fluid containing particulate matter from the top portion with two equal lengths.

In another implementation, an apparatus includes multiple lysing channel structures coupled to each other to pass a fluid containing particulate matter in sequence between the lysing channel structures; a soluble substance coating on at least a portion of the surfaces of the multiple lysing channel structures that, after the fluid is received into the multiple lysing channel structures, diffuses into a portion of the fluid received into the multiple lysing channel structures; and a test chamber to receive the fluid containing particulate matter from the multiple lysing channel structures.

Certain implementations can optionally include one or more of the following features. The fluid that is received into the chamber and the fluid that is received into the multiple lysing channel structures can be different portions of the same fluid sample. The fluid containing particulate matter can be whole blood, and the soluble substance coating can include sodium deoxycholate and at least one additive that, after the soluble substance diffuses into the portion of the whole blood received into the multiple lysing channel structures, prevents an increase in viscosity of the portion of whole blood received into the multiple lysing channel structures. Each of the multiple lysing channel structures can include a substantially straight backbone channel having a base portion; and a top portion with two equal lengths, substantially parallel side channels extending substantially orthogonal to the top portion of the backbone channel. The multiple lysing channel structures can be arranged such that: a first lysing channel structure receives the fluid containing particulate matter at the base portion, and a second lysing channel structure has an end of the base portion coupled to receive the fluid containing particulate matter from the top portion with two equal lengths.

The details of one or more implementations are set forth in the accompanying drawings and the description below.

Certain implementations can provide any of a variety of advantages. For example, the effects of sedimentation can be negated without relying on techniques to agitate a fluid containing particulate matter which, in some contexts, may not be possible. For instance, a microfluidic circuit that includes a chamber or microfluidic channel that holds and dispenses fluid (e.g., whole blood) into the circuit may not be readily agitated, such as through shaking the circuit or mixing/stirring the fluid. Micro-features described in this document can be used to allow for such a fluid to be dispensed with a near constant particle flow rate in spite of ongoing sedimentation.

Other potential features and advantages will become apparent from the description, the drawings, and the claims.

Other implementations of these aspects include corresponding systems, apparatus and computer programs, configured to perform the actions of the methods, encoded on computer storage devices.

BRIEF DESCRIPTION OF THE DRAWINGS

In the drawings, like reference numbers represent corresponding parts throughout.

DETAILED DESCRIPTION

Dispensing fluids containing particulates and performing operations using dispensed fluids, such as cell counting, particularly within micro-environments, can pose various challenges based on, for example, properties of fluids containing particulate matter and/or complexities in quantifying particulate matter. For example, coagulating properties of whole blood (example fluid containing particulate matter), or components of whole blood, can cause it to become inhomogeneous while flowing through microfluidic passages. In another example, sedimentation within a chamber or channel holding whole blood can cause concentrations of blood cells to stratify as time passes. These example factors can cause errors in analytical operations performed on the fluids, such as in cell counting techniques due to non-uniform distribution of cells throughout the microfluidic chambers where measurements can be taken.

This document describes apparatuses, systems, and techniques for holding and dispensing micro-features to mitigate the tendency for particle-laden fluids, for example, whole blood (or whole blood components), to become inhomogeneous under low-shear flow conditions. Such apparatuses, systems, and techniques can be implemented in any of a variety of contexts, such as in disposable cartridges that can be used by analyzer devices to analyze fluids injected into the disposable cartridges, reusable cartridges that can be used by analyzer devices to analyze fluids injected into the reusable cartridges, analyzer devices that can include such micro-features, and/or other appropriate devices/apparatuses/systems.

Figure 1:
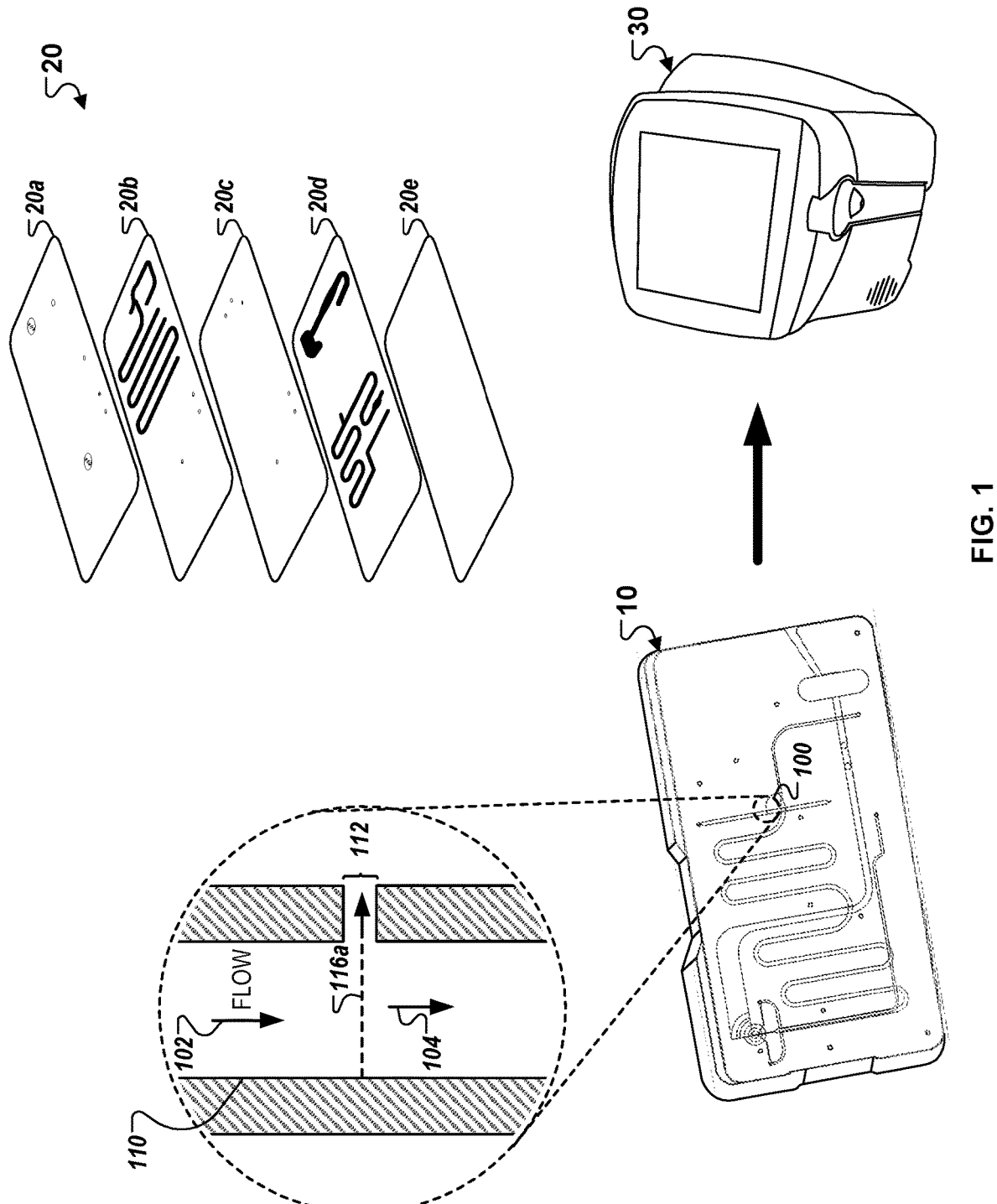
FIG. 1 illustrates components of an exemplary system.

FIG. 1 illustrates components of an exemplary system that uses an example micro-feature to dispense fluid containing particulate matter. The example system that is depicted includes a cartridge 10 that can receive a fluid, such as whole blood (or whole blood components), and that can be inserted into an analyzer device 30 for analysis. The analyzer device 30 can perform various tests on the fluid contained in the cartridge 10 by circulating the fluid within the cartridge 10 in particular ways using fluidic circuits and a dispensing micro-feature 100 that are contained within the cartridge 10. The example micro-feature 100 can include a chamber 110 and an outlet port 112 that permit near uniform fluids containing particular matter to be dispensed into the fluidic circuits and analyzed by the analyzer device 30. The cartridge 10, which can be disposable (e.g., intended for a single use) and/or reusable (e.g., able to be used multiple times without performance degradation), can be, for example, fabricated by attaching one or more laminated sheets 20 containing the channels of the fluidic circuit.

As described in more detail below, the example fluid holding and dispensing micro-feature can include a chamber 110 and an outlet port 112 that is arranged perpendicularly on an outlet plane 116a such that when fluid is inserted into the chamber 110, a portion of the fluid maintains a uniform cell distribution within a particular region of the chamber 110 where the outlet port can be placed. A portion of the fluid within the chamber 110 may then be dispensed through the outlet port 112 in a controlled manner, generating a near constant bulk volumetric flow rate of particulate matter through the outlet port 112. The outlet port 112 can define an opening in a sidewall of the chamber 110 through which fluid in the chamber is dispensed from the chamber 110, for example, into one or more fluidic circuits. The particle dispense rate through the outlet port 112 can be measured to calculate a concentration of the particulate matter within the fluid passing through the chamber 110. In some embodiments, the fluid that is inserted into and dispensed form the chamber 110 can be whole blood or whole blood components. Other particle-laden fluids may also be used with the example micro-feature 100.

The cartridge 10 can be a low-cost apparatus that that can include different types of fluidic circuits that are formed within the cartridge 10, such as through the multiple sheets 20, for analyzing fluid samples during testing procedures. The cartridge 10 can be fabricated using any of a variety of appropriate manufacturing techniques, such as injection molding, embossing, laser ablation, machining, etching, lamination, and/or various combinations of such techniques. The cartridge 10 can also be manufactured using various materials such as metal, metal alloys, silicon, plastics, polymers, and/or various combinations of such materials.

Fluidic circuits within the cartridge 10 can include various regions to receive, process, and output fluid samples during testing procedures. For instance, the fluidic circuits can include a sample inlet for inserting a fluid sample to be analyzed, multiple reagent inlets involved in the testing procedure, a reaction-sustaining channel where a particular reaction is performed to generate results of the testing procedure, and a circuit outlet where the fluid sample and/or other waste products are dispensed from the cartridge 10. Other fluidic circuits and/or features are also possible.

Fluid may be collected and introduced into the cartridge 10 and/or the micro-feature 100 by any suitable technique. For example, a blood sample may be collected from a patient by a finger prick directly on the cartridge 10 such that the blood sample is collected and directly introduced to the cartridge 10 and/or the micro-feature 100. In other exemplary embodiments, blood may be collected by a finger prick and subsequently introduced to the cartridge 10 and/or the micro-feature 100.

In some implementations, the cartridge 10 can be fabricated using a single laminated sheet. In other implementations, the cartridge 10 can be fabricated using a combination of multiple laminated sheets 20 that can be manufactured separately and/or composed of different materials. For example, the multiple laminated sheets 20 can have different structural properties such as, differing levels of rigidity, elasticity, and/or hardness, to improve the overall strength and durability of the cartridge 10. In another example, the multiple laminated sheets 20 can include individual sheets with different flexibilities such that the flexible layers can be used to form a valve structure within the cartridge 10. In other examples, coating materials can be used for certain layers of laminated sheets that include fluidic circuits that are used to perform reactions with reagents and/or fluid samples.

As shown in FIG. 1, in one example implementation, the multiple laminated sheets 20 includes layers 20a-e, to form the single cartridge 10. In such an implementation, the top and bottom layers, 20a and 20e, respectively, can be made from acrylic to increase the overall durability of the cartridge 10. The intermediate layers 20b-d can be made from mylar and can include adhesive tacking to bond the multiple laminated sheets 20. The layers 20b and 20d can include fluidic circuits that can be used alternatively and/or in combination to perform sample analysis. For example, the layer 20b can be used to run a fluid sample and layer 20d can be used to run reagent fluid. In another example, the layer 20a can be used to run a sample, and the layer 20b can be used to collect waste products generated from reactions taking place within the fluidic circuit. Other uses, configurations, compositions, properties, and/or arrangements of the layers 20a-e are also possible.

The analyzer device 30 can be a multi-platform point-of-care device capable of performing multiple clinical diagnostic tests using small fluid sample volumes that are injected into the cartridge 10. The analyzer device 30 can be configured to operate with different types disposable cartridges 10 that are adapted to implement various different detection techniques, such as flow cytometry, electrochemistry, colorimetric analysis, and/or imaging of whole blood or whole blood components. For example, in some instances, the analyzer device 30 can be used to perform electrochemical analyses of analytes within a whole blood sample for a basic metabolic panel (BMP). In other instances, the analyzer device 30 can be used to perform flow cytometry assays for detection of particular types of white blood cells such as CD3, CD4, CD8, and C-reactive proteins (CRP), bead-based assays, reflectance spectroscopy for comprehensive metabolic panel (CMP), and/or imaging for determining a erythrocyte sedimentation rate (ESR).

The analyzer device 30 can also include various subsystems that allows the analyzer device 30 to be used as a single-format testing apparatus for performing commonly-occurring blood tests. For example, the analyzer device 30 may include cellular and/or protein analysis subsystems for performing optical/fluorescence flow cytometry and imaging, electrochemical subsystems, and/or photochemical subsystems for performing reflectance/absorption calorimetry and chemiluminescence. In such examples, the subsystems can be physically and/or logically co-housed within a single apparatus such that the analyzer device 30 can be used with different types of cartridges 10 that are specifically designed for various testing procedures. The example micro-feature 100 can be incorporated into various different types of cartridge designs and can be used to dispense fluids to perform various tests by the analyzer device 30.

The analyzer device 30 can also include a user interface, including a display and input features (e.g., touchscreen, keypad, buttons), that allows healthcare professionals or other users to select experimental tests to be performed by the analyzer device 30, to adjust testing parameters, to insert fluid sample information, to view prior or current test results, and/or to transmit the test results over a network. For example, the analyzer device 30 can be used to perform diagnostic tests in low-resource environments, to provide results to onsite medical professional, and to transmit the generated results to a centralized healthcare infrastructure, such as a hospital and/or an electronic medical record system.

For example, the system depicted in FIG. 1 can be used perform cell counting of particular analytes, such as red blood cells, white blood cells, and/or hemoglobin platelets within a sample of whole blood or whole blood components. For instance, a whole blood sample can be injected into cartridge 10 and received in the chamber 110 as part of the fluid holding and dispensing micro-feature 100. As the whole blood sample is dispensed from the chamber 110 through the outlet port 112, the analyzer device 30 can be used to detect cells that are dispensed through the outlet port 112 and to perform various tests on the dispensed cells. Other uses of the micro-feature 100 and the cartridge 10 by the analyzer device 30 are also possible.

Cartridge 10, analyzer device 30, and/or micro-feature 100 thus provide a compact, efficient and easy to use system that may be readily implemented at a point-of-care location. Such a system may in some embodiments allow a blood sample to be collected, introduced to micro-feature 100, and analyzed, with results available contemporaneously and in an efficient manner. Accordingly, an exemplary system minimizes additional processing steps and associated costs that may otherwise result when a sample must be sent to a dedicated processing laboratory or facility according to traditional analysis techniques. Further, an exemplary system may provide immediate results, increasing the availability of information for a doctor to diagnose and treat a patient, and thus improve overall quality of care.

Figure 2:
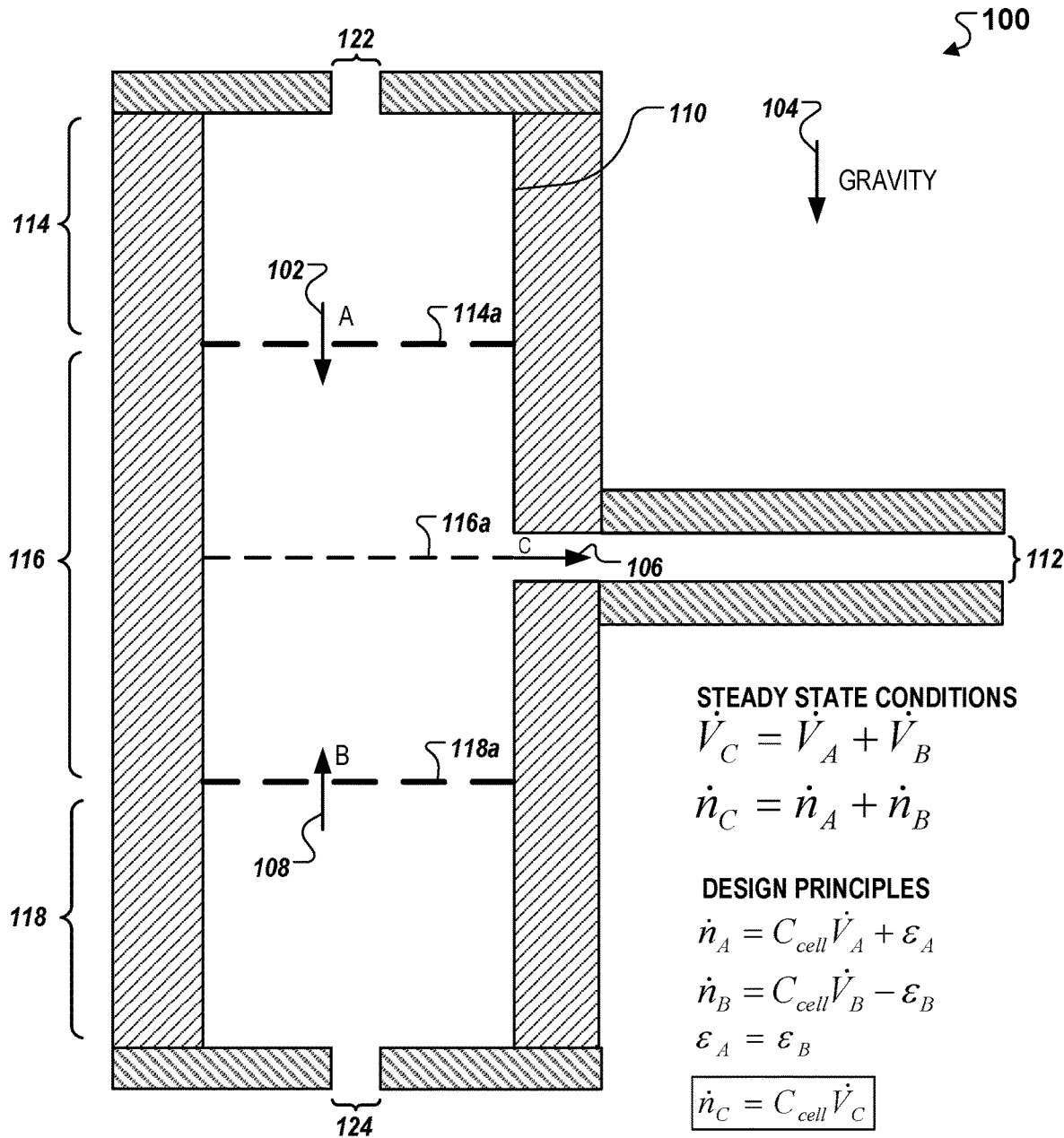
FIG. 2 illustrates design principles of an exemplary fluid holding and dispensing micro-feature.

FIG. 2 depicts a cross-section view of an example fluid holding and dispensing micro-feature 100. As depicted, the example fluid holding and dispensing micro-feature 100 includes a chamber 110 to receive and hold a fluid sample, and an outlet port 112 to dispense the fluid sample from the chamber 110 in a rate-controlled manner. The chamber 110 can act as a sedimentation column such that, after the fluid sample is received by the chamber 110, regions 114, 116, and 118, representing fragmented portions of the fluid sample with varying particulate concentrations within the chamber 110, develop as a result of particle sedimentation from a gravitational force 104. Specifically, particles within the fluid sample are displaced downstream towards the region 118 as time elapses after the fluid is received by the chamber 110.

Implementations of the example fluid holding and dispensing micro-feature 100 may include different inlet ports to receive the sample fluid into the chamber. As depicted, in some implementations, the chamber 110 can be attached to an inlet port 122 that transports the sample fluid into the top region 114. In other implementations, the chamber 110 can alternatively be attached to an inlet port 124 that transports the sample fluid into the bottom region 124. In other implementations, the chamber 110 may also be attached to both the inlet ports 122 and 124.

The example fluid holding and dispensing micro-feature 100 that is designed to observe control-volume principles that conserve physical properties of fluids. For instance, the micro-feature 100 can be designed to conserve energy and mass of the received fluid sample as the fluid sample is displaced through the chamber 110. At steady state, the bulk volumetric flow rate of fluid sample transported into the chamber 110 is equal to the bulk volumetric flow rate of a portion of the fluid sample that is dispensed through the outlet port 112, as shown by equation 1:

$$\dot{V}_C = \dot{V}_A + \dot{V}_B \quad (1)$$

where $\dot{V}_A$ represents the bulk volumetric flow rate of the fluid sample from the top region 114, $\dot{V}_B$ represents the bulk volumetric flow rate of the fluid sample from the bottom region 118, and $\dot{V}_C$ represents the resulting bulk volumetric flow rate of fluid that is dispensed through the outlet port 112.

As the fluid sample is fragmented within the chamber 110 (as a result of sedimentation), the volume of fluid sample within the top region 114, the middle region 116, and the bottom region 118, the sedimentation of particulate matter causes varying distributions of particles within the top region 114, the middle region 116, and the bottom region 118. For instance, the middle region 116 contains volume of fluid sample with a uniform distribution of particulate matter is displaced downstream due to sedimentation. At steady state, the number of individual particles from among the particulate matter of the fluid sample flows through the chamber 110 according to the expression represented by equation 2:

$$\dot{n}_C = \dot{n}_A + \dot{n}_B \quad (2)$$

where $\dot{n}_A$ represents the particle transport rate of fluid sample transported into the chamber 110 from the top region 114, $\dot{n}_B$ represents the particle transport rate of fluid sample transported into the chamber 110 from the bottom region 118, and $\dot{n}_C$ represents the particle transport rate of fluid dispensed through the outlet port 112. Thus, under steady state conditions, the particle transport rate of the fluid dispensed through the outlet port 112 is controlled, resulting in a constant cell dispensing rate from the chamber 110 based on the uniform distribution of particulate matter within the volume of fluid sample within the middle region 116, which remains constant to balanced sedimentation in the upper and lower portions of the chamber 110.

Figure 3:
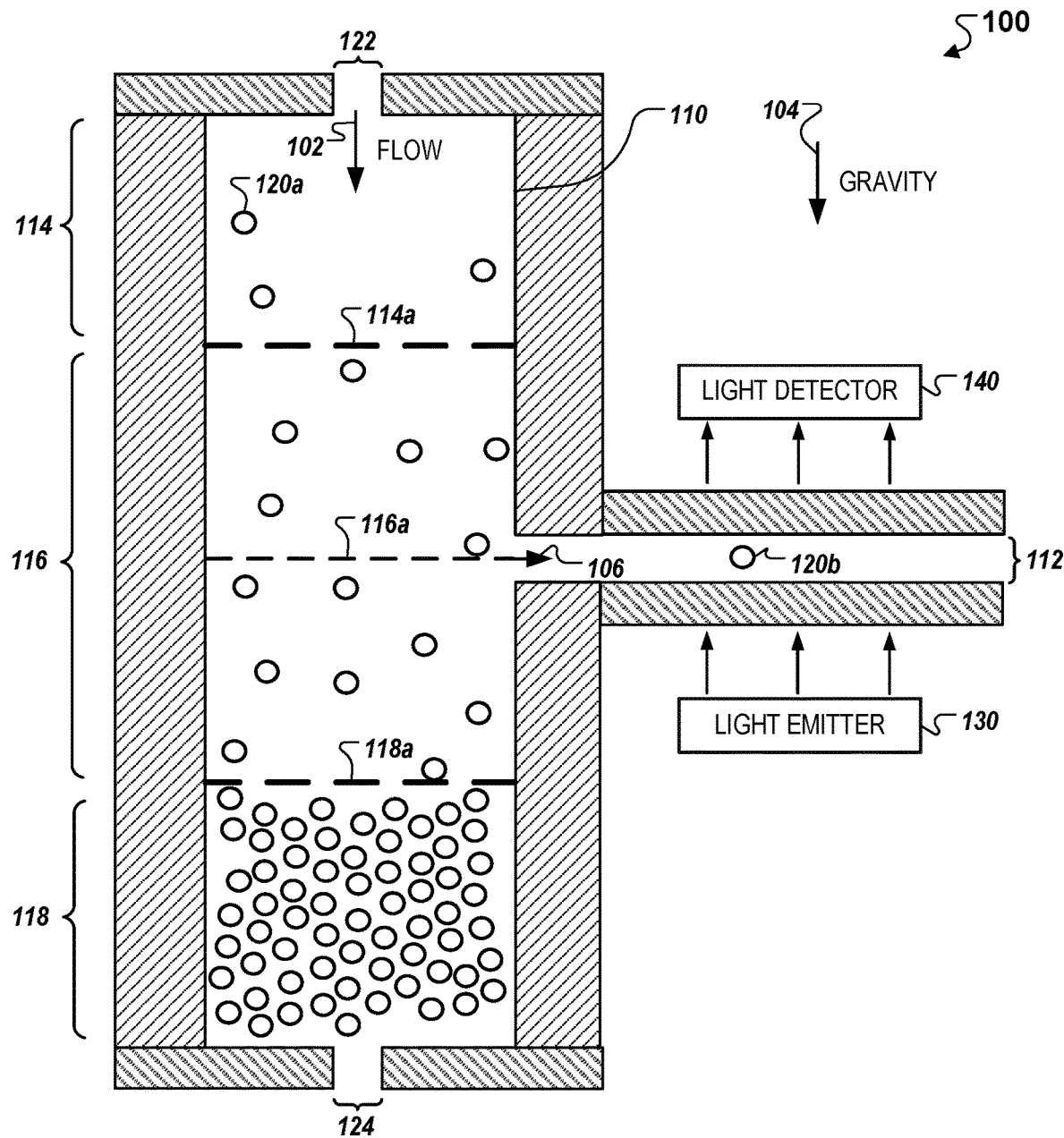
FIG. 3 illustrates a cross-section view of fluid displacement within an exemplary fluid holding and dispensing micro-feature.

FIG. 3 depicts a cross-section view of fluid displacement within an example fluid holding and dispensing micro-feature 100. As shown, the chamber 110 may receive a fluid sample that includes individual particles 120a, and portions of the fluid sample that include particles 120b that are dispensed through the outlet port 112.

The fluid sample can be displaced through the chamber 110 by injecting another fluid (e.g., a reagent fluid, inert fluid) into the chamber 110, which imposes a compression force on the fluid sample that pushes the volume of the fluid sample through the various regions of the chamber 110. In some instances, such another fluid can be injected through an inlet port 122 connected to a portion of the chamber 110 that corresponds to the top region 114, which then displaces the volume of fluid sample inside the chamber 110 from the top region 114 towards the bottom region 118. In such instances, the other fluid can have a lower density of particulate matter relative to the fluid sample.

Additionally and/or alternatively, such another fluid can be injected through a different inlet port 124 connected to a portion of the chamber 110 that corresponds to the bottom region 118, which then displaces the volume of the fluid sample inside the chamber 110 from the bottom region 118 towards the top region 118. In such instances, the reagent fluid has a greater density of particulate matter relative to the fluid sample.

Such another fluid can be injected into the chamber 110 using a fluid actuating device to provide a constant compression force on the fluid sample within the chamber 110. For instance, the actuating device can be configured to inject the other fluid (e.g., reagent fluid) at a particular compression force that ensures that the bulk volumetric flow rate of the fluid sample into the chamber 110 is equal to the bulk volumetric flow rate through an interface 114a between the top region 114 and the middle region 116 to establish steady state conditions as described in FIG. 2. In some implementations, such a fluid actuating device can be located within the analyzer device 30.

In some implementations, the fluid holding and dispensing micro-feature 100 can include multiple inlet ports 122, 124, and/or other inlet ports (not depicted) that are connected to the chamber 110 to support various alternative configurations to inject the fluid sample and the other fluids (e.g., reagent fluids). For example, the fluid sample and the reagent fluid can be injected into the chamber 110 through separate inlet ports 122 and another inlet port (not depicted) that are connected to a portion of the chamber 110 that corresponds to the top region 114. In another example, the fluid sample and the reagent fluid can be injected into the chamber 110 through separate inlet ports 124 and another inlet port (not depicted) that are connected to a portion of the chamber 110 that corresponds to the bottom region 118. In other examples, the fluid sample can be injected through a first inlet port 122 that is connected to a portion of the chamber 110 that corresponds to the top region 114 whereas the reagent fluid can be injected through a second inlet port 124 that is connected to a portion of the chamber 110 that corresponds to the bottom region 118, and vice versa.

In some implementations, the fluid holding and dispensing micro-feature 100 can include other outlet ports (not depicted) that are connected to the chamber 110 to support various alternative configurations to dispense the fluid sample and the other fluids (e.g., reagent fluids). For example, the fluid sample and the reagent fluid can be dispensed from the chamber 110 through separate outlet ports placed on different vertical sidewalls of the chamber 110 along the plane 116a such that the dispensed sample fluid flow through the multiple outlet ports 112 has a normal vector substantially perpendicular to gravity. In other examples, the multiple outlet ports 112 can be placed on different planes of the chamber 110 such that sample fluid and the reagent fluid can be dispensed from different regions of the chamber 110 over different periods of time.

As discussed in FIG. 2, as the fluid sample is displaced through the chamber 110, fractions of the fluid sample develop due to the sedimentation of particulate matter within the fluid sample by the gravitational force 104. This causes the fragmentation of the fluid sample into the top region 114, the middle region 116, and the bottom region 118. As shown, the regions 114-118 are segmented by interfaces 114a and 118a. The volume of fluid sample within the top region 114 includes a low concentration of particles 120a due to the gravitational force 104 causing the particles 120a to sediment downstream towards the bottom region 118. The middle region 116 includes a volume of fluid sample that has a homogenous concentration of the particles 120a. For example, the volume of fluid sample within the middle region 116 may have a uniform cell distribution such that the particles 120a. The bottom region 118 includes a packed layer that has the greatest concentration of particulate matter within the chamber 110. For instance, in examples where the fluid sample is whole blood or whole blood components, sedimentation can cause the top region 114 to contain a plasma supernatant of the whole blood, the middle region 116 to contain pristine blood with concentrations of blood cells that are the same or similar as concentrations when the whole blood was first received in the chamber 110, and the bottom region 118 can contain a packed cell layer with the greatest concentration of cells.

The outlet port 112 is positioned along a portion of the chamber 110 that corresponds to the middle region 116 to ensure that fluid that is dispensed from the chamber 110 has a constant state, which can allow for tests performed using the dispensed fluid to be more accurate and consistent than if fluid were dispensed from either the top region 114 or the bottom region 118. This arrangement of the chamber 110 and the outlet port 112 allows for controlled cell dispensing through the outlet port 112, which is can then be subsequently used to calculate the particulate concentration of the fluid sample within the chamber 110 based on the design principles described in FIG. 2. For instance, since the outlet port 112 is substantially perpendicular to the gravitational force 104, gravity-induced sedimentation within the chamber 110 does not impact the transport of dispensed fluid sample and individual particles 120b through the outlet port 112.

As shown in FIG. 3, as the fluid sample is displaced through the chamber 110 according to a bulk flow 102 that is parallel to gravity, the particles 120a within fluid can be displaced from the top region 114 downstream to the bottom region 118 by the bulk flow 102. As time elapses, three phases of the fluid sample, represented by regions 114-118, generate within chamber 110 due to particulate sedimentation.

Under steady state conditions, as described in FIG. 2, the bulk volumetric flow rate and the particle transport rate of the portion of the fluid sample within the chamber 110 that is dispensed through the outlet port 112 are used to determine the particulate concentration of the fluid sample within the chamber 110. The portion of the fluid sample that is dispensed through the outlet port 112 can be analyzed using the analyzer device 30 as described in FIG. 1. For example, in some instances, the analyzer device 30 can be used to measure a bulk volumetric flow rate and a particle transport rate (or a cell dispense rate), represented by the volume of fluid sample and the number of particles, respectively, that is dispensed through the outlet port 112 over a particular period of time. The analyzer device 30 may use various detection techniques to determine the presence of individual particles 120b within the outlet port 112. For example, in some implementations, as shown in the example in FIG. 3, the analyzer device 30 may use optical techniques to detect light scattering events that indicate the presence of particles 120b within the outlet port 112. In such implementations, the analyzer device 30 may include a light emitter 130 that illuminates a channel connected to the outlet port 112 such that as the particles 120b pass through the channel, a light detector 140 that collects a detection signal based on the number of scattering events over a particular period of time. In other implementations, alternative detection techniques can be used to detect the presence of the particles 120b through the outlet port 112.

The analyzer device 30 can be used to calculate the particulate concentration of the fluid sample that is dispensed through the outlet port 112, for example, based on the expression shown in equation 3:

$$\dot{n}_{outlet} = C_{cell} \times \dot{V}_{outlet} \qquad (3)$$

where $\dot{n}_{outlet}$ represents the particle transport rate (or cell dispense rate) of the portion of the fluid sample that is dispensed through the outlet port 112, $C_{cell}$ represents the particulate concentration of the portion of the fluid sample that is dispensed through the outlet port 112, and $\dot{V}_{outlet}$ represents the volumetric flow rate of the portion of the fluid sample that is dispensed through the chamber 110. As shown in equation 3, the cell dispense rate through the outlet port 112 is equal to the product of the particulate concentration of the fluid sample dispensed through the outlet port 112 and the bulk volumetric flow rate of the flow 106. Using this expression, the measured cell dispense rate, determined by the number of individual cells dispensed through the outlet port 112 over a particular period of time, and the measured volumetric flow rate, determined by the volume of fluid sample that is dispensed through the outlet port 112 over the particular period of time, can be used to calculate the cell concentration of the dispensed portion of the fluid sample.

In some implementations, the fluid sample that is received by the chamber 110 can be whole blood or whole blood components. In such implementations, the fluid holding and dispensing micro-feature 100 can be used, for example, to calculate cell concentrations of analytes within whole blood such as, for example, red blood cells, white blood cells and platelet cells, without substantial pre-processing steps to homogenize whole blood. For example, whole blood can be injected into the fluidic circuit of the cartridge 10, which includes the fluid holding and dispensing micro-feature 100. More specific details related to use of whole blood within the fluid holding and dispensing micro-feature 100 is discussed in FIGS. 5-7.

The micro-feature 100 that is described with regard to and depicted in FIGS. 2-3 can be implemented in a cartridge, such as the example cartridge 10 (e.g., disposable cartridge, reusable cartridge), that is used and controlled by another device, such as the analyzer device 30, to perform various tests on the fluid contained and dispensed by the micro-feature 100. In other implementations, the micro-feature 100 can be incorporated into devices that are performing one or more portions of the analyzing techniques. For example, the micro-feature 100 can be incorporated into the analyzer device 30. Other implementations of the micro-feature 100 are also possible.

Figure 4:
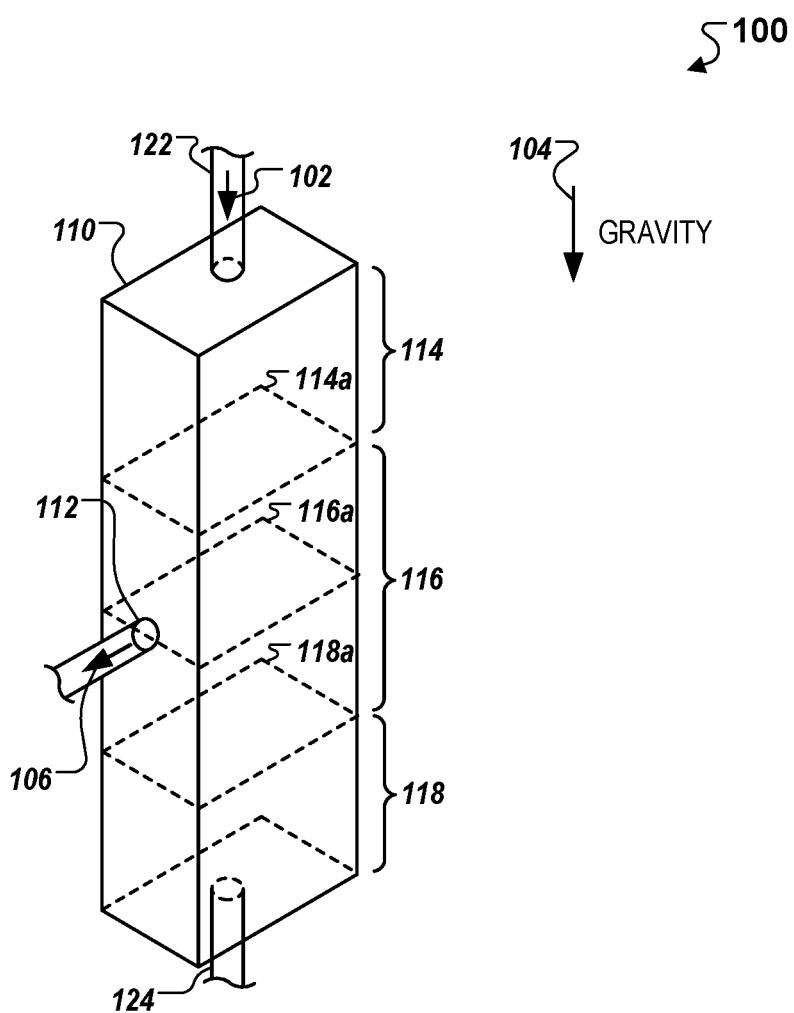
FIG. 4 illustrates a perspective view of an exemplary fluid holding and dispensing micro-feature.

FIG. 4 illustrates a perspective view of an example fluid holding and dispensing micro-feature 100. As shown, the chamber 110 can be enclosed with four vertical sidewalls that form a rectangular chamber 110 along the longitudinal axis of the cartridge 10. In other implementations, other three-dimensional shapes which are of substantially constant cross section, such as, triangular prism and/or cylindrical shapes, can be used as long as the opening of the outlet port 112 that meets the chamber 110 has a normal vector substantially perpendicular to gravity when the micro-feature 100 is positioned to be dispense fluid from within the chamber 110 (e.g., when the cartridge 10 is inserted into the analyzer device 30).

Figure 5:
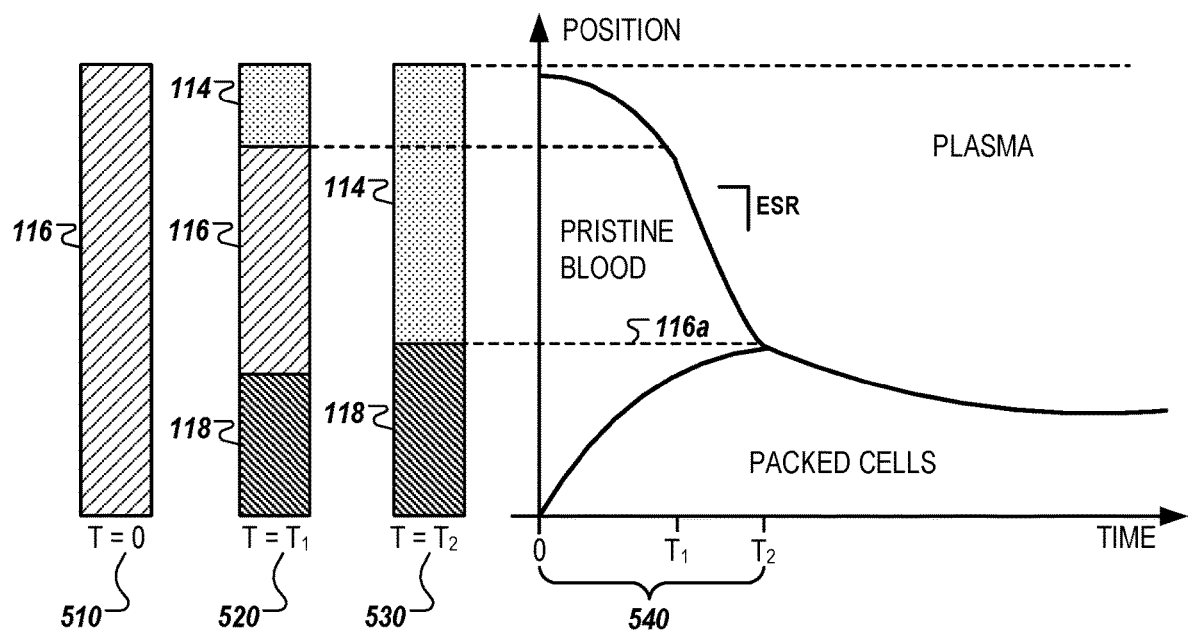
FIG. 5 is a phase diagram representing the spatial content of a sedimenting body of whole blood.

FIG. 5 is a diagram representing the spatial content of an example sedimenting body of whole blood during various time points after injection into the chamber 110. For instance, the diagram 500 represents the vertical position of fractions of whole blood within the chamber 110 as a function of time after the whole blood has been inserted into the chamber 110. As shown, at time point 510, "T=0," the chamber 110 contains only pristine blood, which represents an initial homogenous state of whole blood prior to sedimentation of particulate matter. As time elapses, for example, at time point 520, "T=$T_1$," particulate matter of the whole blood begins to sediment, generating three phases within the microfluidic channel—a cell-deplete plasma supernatant layer that eventually occupies the top region 114, a packed cell layer that eventually occupies the bottom region 118, and a sustained region of pristine blood that separate the plasma supernatant and the packed cell layer within the middle region 114. The vertical height of the pristine blood layer within the chamber 110 reduces as particulate matter within whole blood sediments until at the time point 530, "T=$T_2$," when the supernatant layer collides with the packed cell layer.

The time period between time points 510 and 530, shown as time period 540, represents the total period for which pristine blood layer occupies the middle region 116 of the chamber 110 after inserting whole blood. The duration of the time period 540 can be impacted by the Erythrocyte Sedimentation Rate (ESR), which reflects the rate of sedimentation of whole blood within one hour. In some example implementations, the time period 540 can be between five minutes to three hours depending on the length of the chamber 110.

To ensure that the bulk volumetric flow rate of particles flowing through the outlet port accurately represent the concentration of the particulate matter within whole blood, fluid can be limited to being dispensed by, for example, the micro-feature 100 from within the time period 540 so that only particles from pristine blood layer are analyzed. This ensures that flow through the outlet port 112 results from homogenized fluid with a uniform particulate concentration from the middle region 116 of the chamber 110. As discussed, the fluid holding and dispensing micro-feature 100 provides a technique to inferentially calculate particulate concentration without requiring substantial pre-processing of whole blood, such as centrifugation, dilution, or other techniques that are commonly used in cell counting.

The micro-feature 100 can be configured so that the outlet port 112 is positioned longitudinally along a sidewall of chamber 110 to correspond to the plane 116a that corresponds to the position at which the top region 114 will meet the bottom region 118 at time point 530 (when "T=$T_2$"). For example, the outlet port 112 can extend from one or more sidewalls of the chamber 110 at a vertical position that corresponds to the plane 116a at which the top region 114 and the bottom region 118 meet at time point 530. By positioning the outlet port 112 at this location (corresponding to plane 116a), the micro-feature 110 can maximize a volume of homogenous fluid that can be dispensed by the micro-feature before sedimentation reduces the fluid to only the top and bottom regions 114 and 118, respectively. The plane 116a, and the corresponding position for the outlet port 112, can be different for different types of fluids and/or different types of particulate matter. The plane 116a and the corresponding position for the outlet port 112 can be determined using any of a variety of appropriate techniques for different types of fluids and/or particulate matter, such as through known rates of segmentation for different types of fluids (e.g., the erythrocyte sedimentation rate for whole blood), empirical evidence from testing under use conditions (e.g., sedimentation rate when within the micro-feature 100), and/or other appropriate techniques. In instances in which empirical evidence is used, any of a variety of different statistical operations can be performed on the empirical evidence to determine the plane 116a and the corresponding position for the outlet port 112, such as average values, median values, and/or other appropriate values.

The analyzer device 30 can be configured to determine the time point 530 at which fluid should stop being dispensed from the chamber 110 and through the outlet port 112. The analyzer device 30 can make such a determination based on any of a variety of appropriate techniques. For example, the analyzer device 30 can determine when the time point 530 has been reached for a particular fluid sample that is located in the cartridge 10 based on the calculated particulate concentration of the whole blood that is dispensed through the outlet port 112. For instance, because the cell dispense rate is dependent on particulate concentration, as shown by equation 3, the measured particulate concentration can be compared to a threshold particulate concentration is associated with the packed cell layer of whole blood. In such instances, in response to calculating a particulate concentration of whole blood that is dispensed through the outlet port 112 that is higher than the threshold particulate concentration, the analyzer device 30 may stop dispensing the whole blood from the chamber 110.

In another example, the analyzer device 30 can determine when the time point 530 has been reached and the fluid sample should stop being dispensed from the cartridge 10 based on an amount of time that has elapsed since the fluid was injected into the chamber 110 and a threshold amount of time, for the particular fluid and the particular micro-feature 100, that corresponds to the time period 530. For example, the analyzer device 30 may have predetermined values for the time period 530 that are specific to various fluids, particulate matter, and/or micro-feature 100 configurations. The analyzer device 30 can identify when a corresponding time period 530 has been met based on an amount of time that has elapsed since the fluid was injected into the chamber 110 of the cartridge 10. The amount of time that has elapsed can include an amount of time since the cartridge 10 was inserted (or otherwise made accessible to) the analyzer device 30, and an amount of time between when the fluid was be injected into the cartridge 10 and when the cartridge 10 was inserted into the analyzer device 10. The latter time period (time between injection of fluid and insertion into analyzer device 30), can be timed by the analyzer device 30 (e.g., medical professional can provide input (e.g., button press, verbal input) indicating when injection is occurring) and/or estimated by the analyzer device 30 (e.g., average time for medical professional to perform injection and insertion steps).

Figure 6:
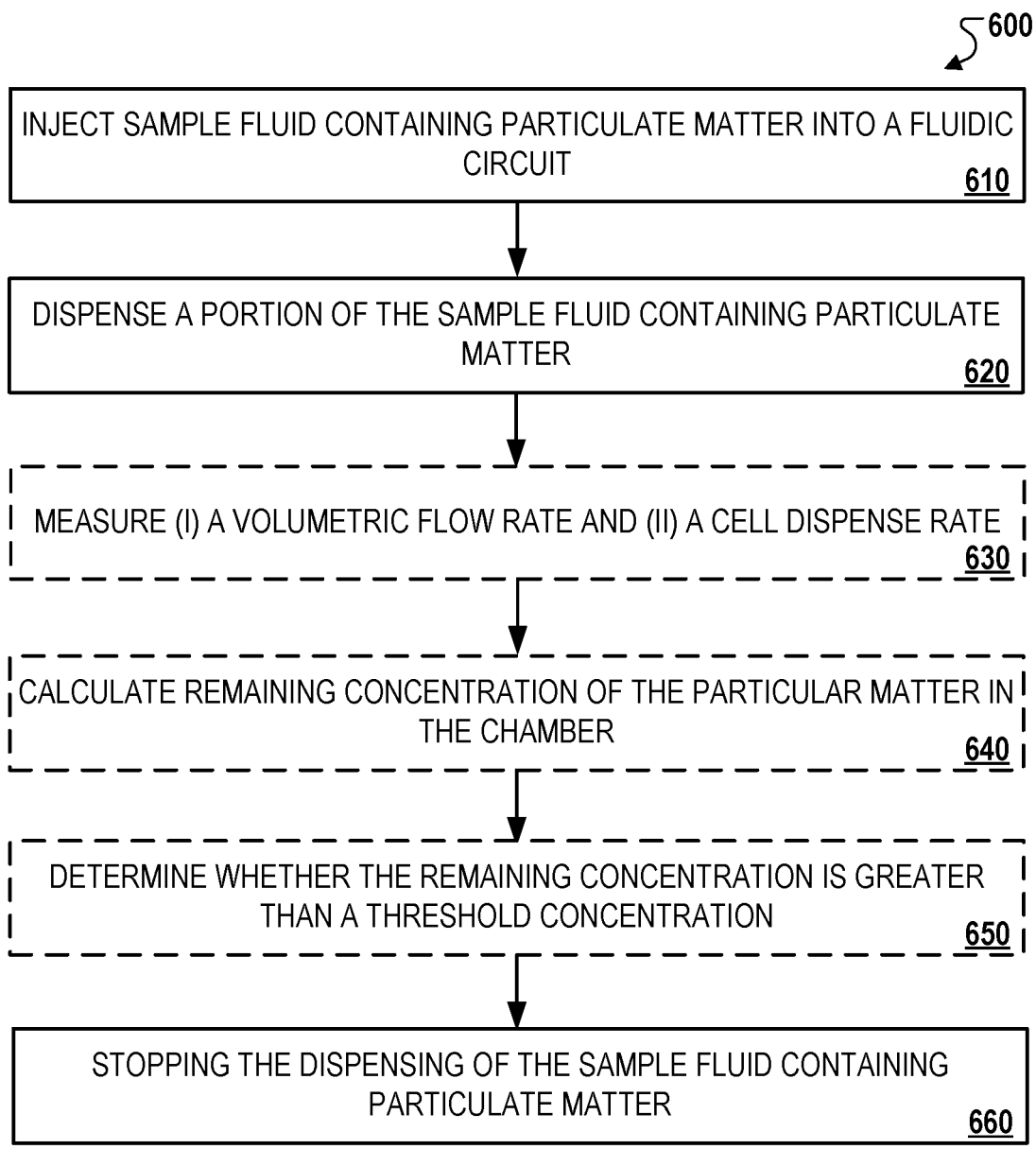
FIG. 6 illustrates an exemplary process for holding and dispensing fluid.

FIG. 6 is a flowchart of an example technique 600 for holding and dispensing fluid. Briefly, the example technique 600 includes injecting fluid containing particulate matter into a fluidic circuit (610), dispensing a portion of the fluid containing particulate matter (620), and stopping the dispensing of the fluid containing particulate matter (660). In some implementations, the technique 600 may optionally include measuring (i) a volumetric flow rate, and (ii) a cell dispense rate (630), calculating a remaining concentration of the particulate matter in the chamber (640), and determining whether the remaining concentration is greater than a threshold concentration (650).

In more detail, the technique 600 includes injecting fluid containing particulate matter into a fluidic circuit (610). For example, whole blood (or whole blood components) can be injected into the fluidic circuit of the cartridge 10, which includes the chamber 110 that has one or more surfaces that define a volume to receive the whole blood. As described previously in FIGS. 3 and 5, after a certain time period from when the whole blood enters the chamber 110, the chamber 110 may include a top region 114 that contains plasma supernatant, a middle region 116 that contains pristine blood, and a bottom region 118 that contains packed cells due to sedimentation.

The technique 600 also includes dispensing a portion of the fluid containing particulate matter (620). For example, a portion of the whole blood that contains pristine blood can be dispensed from the middle region 116 into the outlet port such that the flow of the dispensed whole blood is substantially perpendicular to gravity. As described in FIG. 3, the pristine blood that is dispensed from the middle region 116 contains a homogenous concentration of red blood cells, which results in a constant particle transport rate of cells that are dispensed through the outlet port 112.

In some implementations, the technique 600 can also include measuring (i) a volumetric flow rate, and (ii) a cell dispense rate (630). For example, the analyzer device 30 can be used to determine a volumetric flow rate corresponding to the volume of whole blood that is dispensed through the outlet port 112 over a period of time after the whole blood is received by the chamber 110.

The analyzer device 30 may also be used to determine a cell dispense rate corresponding the number of individual red blood cells that are dispensed through the outlet port 112. For instance, as described in FIG. 3, in some implementations, the analyzer device 30 may include the light emitter 130, which illuminates the pathway connected through the outlet port 112, and the light detector 140, which detects a number of scatter events over a particular period of time after the whole blood is received by the chamber 110. In such instances, the light emitted by the light emitter 130 can be scattered by individual red blood cells, and the light detector may determine the number of red blood cells passing dispensed through the outlet port based on the number of scattering events.

In some implementations, the technique 600 can also include calculating a remaining concentration of the particulate matter (640). For example, the analyzer device 30 can calculate a remaining concentration of red blood cells within the chamber 110 based on the measured volumetric flow rate and the cell dispense rate through the outlet port 112. As discussed in FIG. 3, under steady state conditions, the cell dispense rate through the outlet port 112 can be related to the red blood cell concentration and the volume of whole blood ejected from chamber 110 using equation 3.

In some implementations, the technique 600 can also include determining whether the remaining concentration is greater than a threshold concentration (650). For example, the analyzer device 30 can be used to determine whether the remaining concentration of red blood cells of the whole blood that is being dispensed through the outlet port 112 greater than a threshold concentration. For instance, the threshold concentration can be the concentration of red blood cells in the packed cell layer of whole blood contained in the bottom region 118 of the chamber 110.

In some implementations, after determining that the red blood cell concentration of the whole blood being dispensed through the outlet port 112 exceeds the threshold concentration, the analyzer 30 can stop the dispensing based on determining that pristine blood is no longer being dispensed through the outlet port 112. As discussed in FIG. 5, the time point associated with when the red blood cell concentration of the whole blood exceeds the threshold concentration corresponds to the time point 530.

The process 600 can include stopping the dispensing of the fluid containing particulate matter (660). For example, dispensing of the whole blood through the outlet port 112 can be stopped after a specified time period when the chamber 110 contains only plasma supernatant or packed cells. As described previously in FIG. 5, after the time period 540, the whole blood within the chamber 110 only contains plasma supernatant and a packed cell layer. After this time period, dispensing can be stopped because the whole blood within the chamber 110 may not have a uniform distribution of red blood cells, which may cause errors in concentration calculations described by equation 3.

In some implementations, dispensing can be stopped in response to determining that pristine blood is no longer being dispensed through the outlet port 112. For instance, the analyzer device 30 may initially calculate the red blood cell concentration of the whole blood being dispensed through the outlet port 112 and then compare the calculated red blood cell concentration to a threshold concentration associated with the red blood cell concentration of the packed cell layer of the whole blood. If the calculated red blood cell concentration exceeds the threshold concentration, then the analyzer device 30 may determine that only whole blood that includes the packed cell layer is being dispensed through the outlet port 112.

Figure 7A:
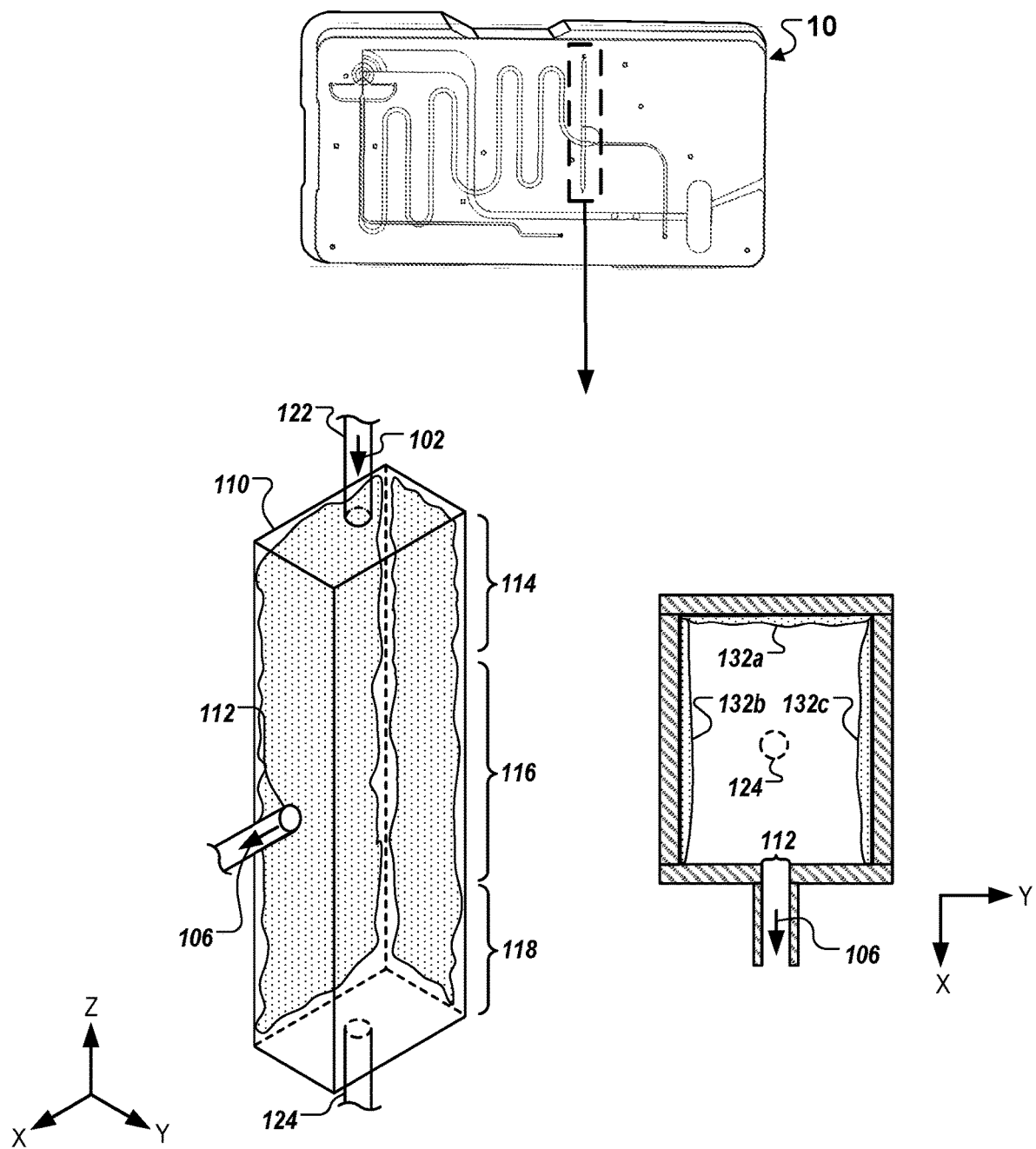
FIGS. 7A-7C illustrate perspective views of exemplary fluid holding and dispensing micro-features with soluble substance coatings deposited in various locations.
Figure 7B:
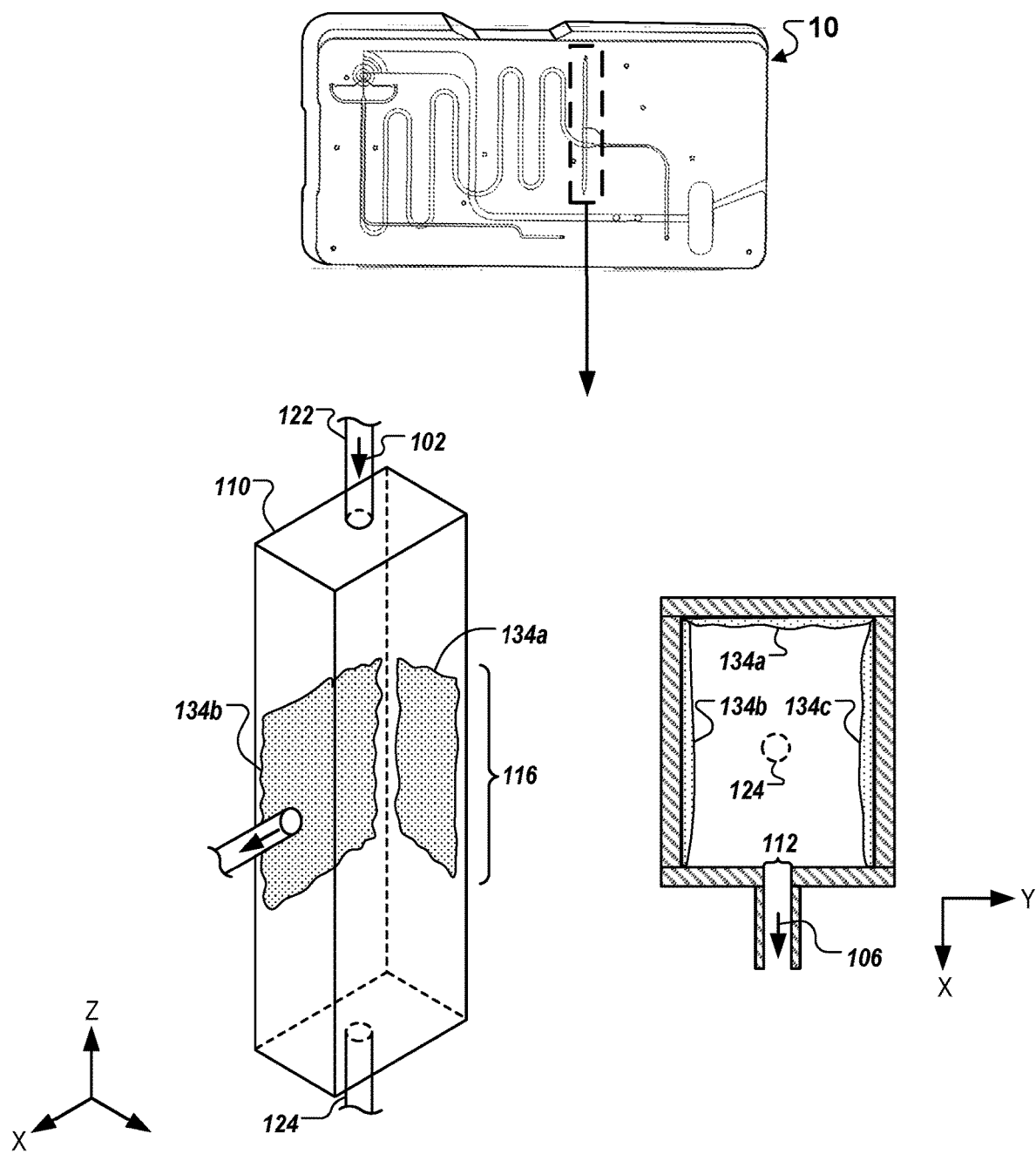
Figure 7C:
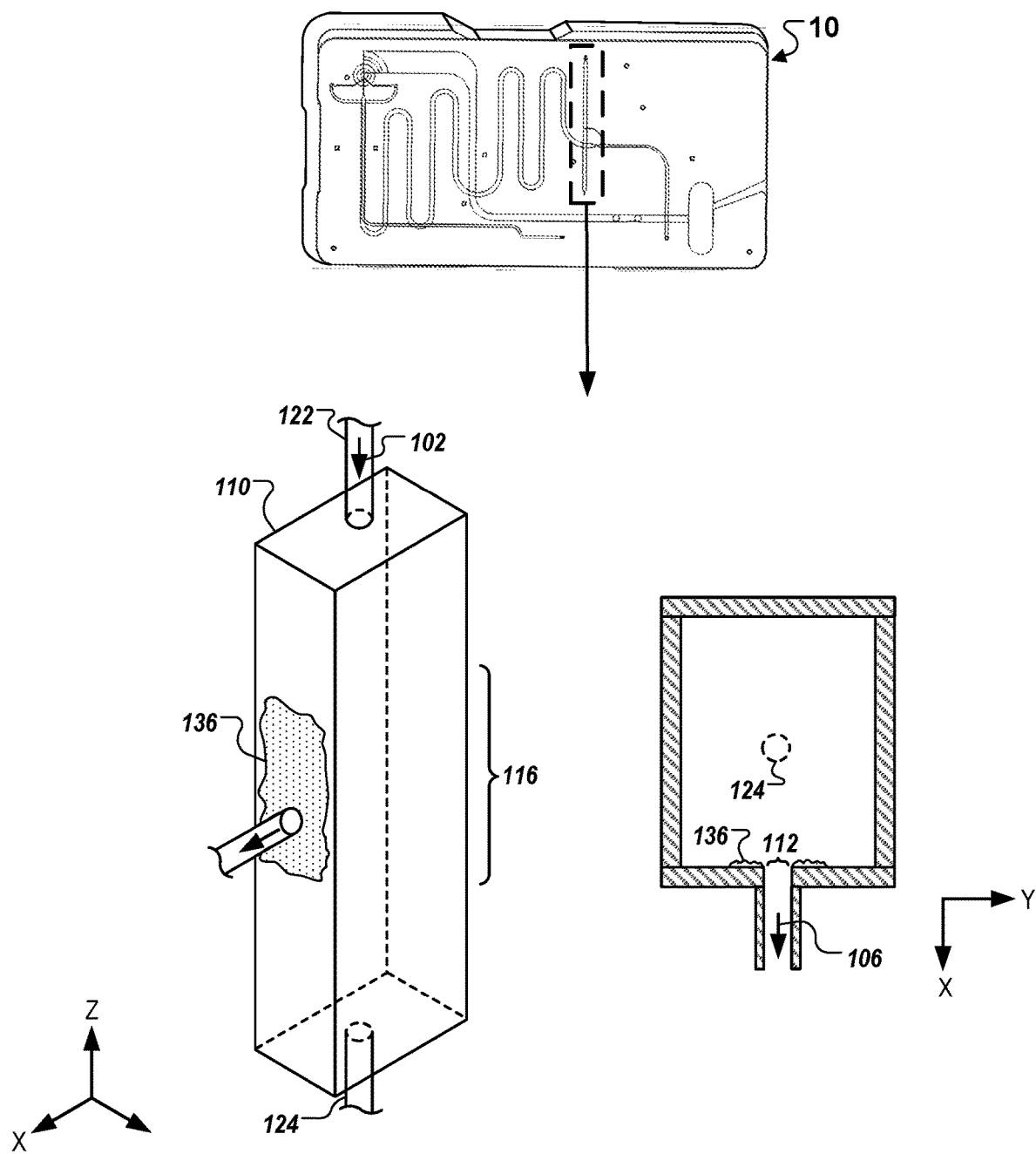

FIGS. 7A-7C illustrate perspective views of exemplary fluid holding and dispensing micro-features with soluble substance coatings deposited in various locations. FIG. 7A illustrates an exemplary implementation of the micro-feature 100 in which an example soluble substance is deposited on the entirety of multiple surfaces of the chamber 110 illustrated in FIG. 4. FIG. 7B illustrates an exemplary implementation of the micro-feature 100 in which an example soluble substance is deposited on portions of multiple surfaces on the chamber 110. FIG. 7C illustrates an exemplary implementation of the micro-feature 100 in which an example soluble substance is deposited on a surface from which the outlet port 112 extends.

In general, one or more soluble substances can be deposited on one or more surfaces of the micro-feature 100 and/or the chamber 110, such as through being dissolved in a carrier fluid such as methanol that is applied to the one or more surfaces, where the carrier fluid is subsequently evaporated to leave behind the dried reagent. In some instances, such a reagent may be stable at room temperature. In some instances, the reagent may be temperature sensitive. In such instances, other techniques such as lyophilization may be performed to improve the room temperature shelf life of the dried reagent.

In operation, a carrier fluid with soluble substance dissolved may be dispensed onto one or more surfaces of the chamber 110. The fluid substance may be evaporated to create a dried substance coating on the one or more surfaces where the carrier fluid was dispensed. Once a sample fluid is introduced into the chamber 110, interaction between a portion of the sample fluid that comes into contact with portions of the surfaces where the carrier fluid was deposited causes the soluble substance to penetrate and/or diffuses into the fluid sample. The location where the carrier fluid and the one or more soluble substances are deposited may therefore be selected to maximize the interaction of the one or more soluble substances and the sample fluid to achieve, for instance, optimal fluorescent tagging as described below.

The concentration and/or amount of the one or more soluble substances deposited onto the surfaces of the chamber 110 may be adjusted based on a variety of factors, such as the volume of the carrier fluid as depicted in the illustrated examples of FIGS. 7A-7C. In some instances, the reagent may be dispensed to multiple surfaces of the chamber 110 to increase the concentration of the soluble substance deposited (e.g., as shown in FIGS. 7A-7B). In other instances, the reagent may only be dispensed to a single surface of the chamber 110 (e.g., as shown in FIG. 7C). Various configurations and concentrations of the one or more soluble substances being deposited onto surfaces of the chamber 110 are possible, such as the example configurations depicted and described with regard to FIGS. 7A-C, as well as other configurations that are not explicitly depicted or described. Additionally, various soluble substances can be deposited onto surfaces of the chamber 110, such as a single soluble substance deposited onto some or all surfaces of the chamber 110, multiple soluble substances deposited onto some or all surfaces of the chamber 110, a first soluble substance being deposited onto some surfaces of the chamber 110 and a second soluble substance being deposited onto other surfaces of the chamber 110, and/or other configurations. Soluble substances can be deposited before, during, and/or after the chamber 110 is assembled as part of the card 10. For example, the chamber 110 may be formed out of multiple layers of material. The one or more soluble substances may be deposited on various portions and/or surfaces of these layers before, during, and/or after the layers are assembled to form the chamber 110.

The volume of the reagent deposited on each surface may also be altered to adjust the concentration and/or amount of the one or more soluble substances deposited. For instance, in the exemplary implementation illustrated in FIG. 7A, reagent is dispensed onto the entirety of three surfaces of the chamber 110 to generate soluble substance coatings 132a-132c. In this example, the concentration and/or amount of the soluble substance to be diffused into the sample fluid introduced into the chamber 110 is increased by maximizing the surface area over three of the surfaces of the chamber. Alternatively, in the exemplary implementation illustrated in FIG. 7B, reagent is dispensed onto only portions of the surfaces corresponding to middle region 116 to generate soluble substance coatings 134a-134c. In contrast, in the exemplary implementation illustrated in FIG. 7C, reagent is only dispensed onto a portion of a single surface. The example surface coatings depicted in FIGS. 7A-C can be combined to form additional and/or alternate implementations, and other implementations are also possible. For example, all four vertical surfaces of the chamber 110 can be coated with a soluble substance (e.g., FIG. 7A with the vertical surface with the outlet port 112 additionally being coated).

The reagent dispense locations can be used to maximize the interaction between the soluble surface coatings and the sample fluid introduced into the sample chamber 110. For example, in FIG. 7B, the soluble substance coatings 134a-134c are placed in portions of the chamber surfaces that coincide with the region 116 based on this region including a homogenously distributed portion of the sample fluid that is then dispensed from the chamber 110 via the outlet 112. In this example, the location of the coatings 134a-134c are selected to maximize interactions only with portions of the sample fluid that are to be analyzed and not the other portions in regions 114 and 118 which either include lysing fluids and/or sediments of particulate matter. In some implementations, the reagent dispense location may be selected to minimize the interaction between the soluble substance coating and lysing or sphering fluid used during a flow cytometry protocol because such interactions cause the soluble substance to be washed away instead of penetrating and/or diffusing into the sample fluid.

The volume of reagent dispensed can be used to minimize the cost associated with manufacturing the microchip 10 by reducing necessary reagent volumes. For example, in FIG. 7C, the coating 136 is only placed on a surface from which the outlet port flows and encompassing an area surrounding the outlet port 112. In this example, the placement of the coating 136 is selected to improve the probability tagging of particulate matter that is included in the portion of the sample fluid that is dispensed through the outlet port 112 while also minimizing the total volume of reagent required to do so (e.g., by limiting dispensing to a single surface compared to the examples depicted in FIGS. 7A-7B).

The techniques described above with respect to FIGS. 7A-7C can be used, for example, to improve the differentiation of eosinophils from other white blood cell populations in a sample of whole blood or whole blood components using flow cytometry techniques. For example, the reagent can be a dried down reagent that includes a concentration of a neutral red dye used to selectively tag eosinophil cells with a fluorescent signal. The neutral red dye may be used to measure fluorescent signals produced from tagged eosinophils to differentiate from other leukocytes using various flow cytometry techniques as described above. The neutral red dye is able to preferentially translocate into the acidic compartments of eosinophils and produce a differential fluorescence signal when excited with, for instance, a 488 nm or 450 nm laser. In one particular implementation, the concentration of neutral red within the dispensed reagent coating is set to around 225 µL/mL in order to maximize the fluorescence signal of the eosinophils while minimizing potential noise from non-specific fluorescent emission (e.g., fluorescently-tagged white blood cells other than eosinophils). At this or similar concentrations, the signal-to-noise ratio of the fluorescent signal is also high enough to differentiate between eosinophils and other white blood cell populations in whole blood (or whole blood components).

In some implementations, various reagents with different soluble substances may be deposited onto the surfaces of the chamber 110 to enable the detection of multiple cellular types. For example, soluble substances deposited onto the surface of the chamber 110 can include one or more of: auramine-o or thiazole orange (which can be used for the detection of reticulocytes), propidium iodine (which can be used for the detection of nucleated red blood cells), and/or different antibodies (which can be used for detecting cellular markers (e.g., CD3, CD4, CD8, CD45, CD123, CD193)). Additionally and/or alternatively, soluble substances can be a synthetically created room temperature stable aptomer that is capable of binding to specific protein sequences or cellular targets.

In some implementations, reagents with different soluble substances may be deposited onto different locations of the chamber 110 to enable the performance of an integrated assay for multiple cellular targets of a single fluid sample. For example, a neutral red reagent may be dispensed onto one surface of the chamber 110 for the detection of eosinophils, whereas a propidium iodine reagent may be dispensed onto another surface of the same chamber 110 for the detection of nucleated red blood cells. In this example, a single whole blood sample may simultaneously analyzed within the chamber 110 for both eosinophils and nucleated red blood cells using flow cytometry techniques. Other combinations of soluble substances are also possible.

Figure 8A:
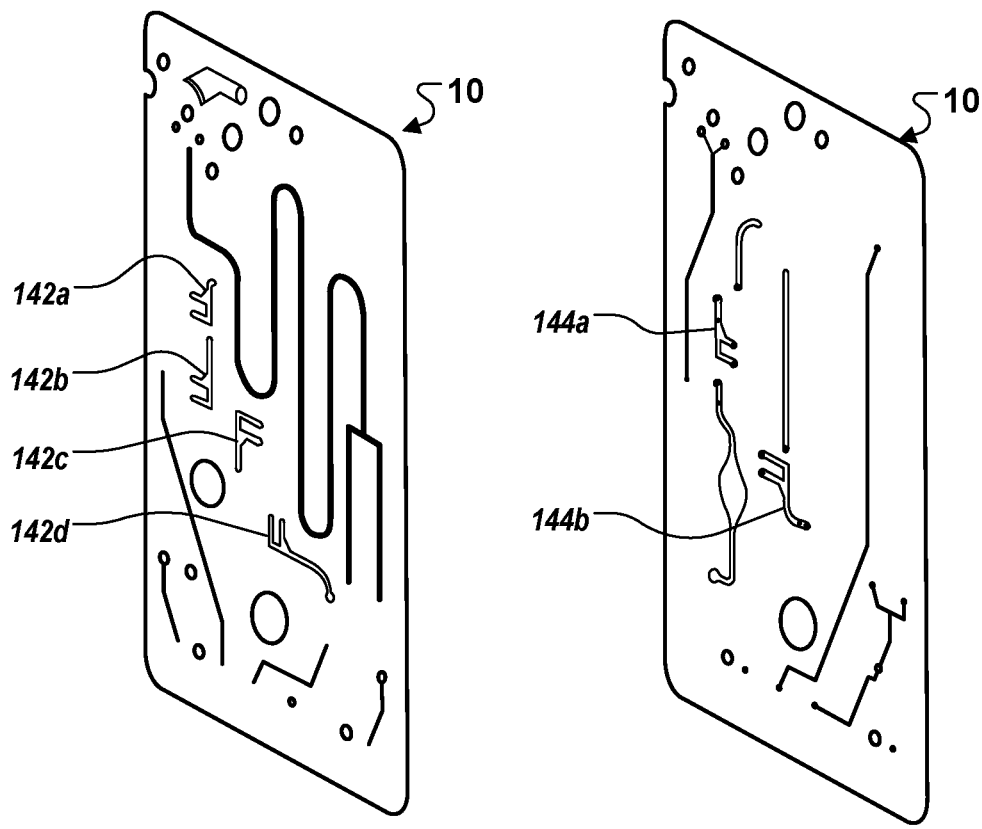
FIG. 8A illustrates perspective views of exemplary microchip layers and that include portions of fluid structures to aid in lysing red blood cells.

FIG. 8A illustrates perspective views of exemplary layers 12 and 13 of a microfluidic cartridge that include portions of fluid structures 142-142d and 144a-144b, respectively, to aid in lysing red blood cells. The layers 12 and 13 may be coupled to each other to form a fluidic circuit that includes lysing channel structures 142-142d and 144a-144b illustrated in FIGS. 8A-8C. The fluidic circuit formed by the layers 12 and 13 may be used to measure hemoglobin in a sample of whole blood (or whole blood components) by utilizing a reagent to aid in the lysis of red blood cells to release hemoglobin into a solution from the whole blood sample. The lysing channel structures 142-142d and 144a-144b may be used to diffuse red blood cells in the whole blood sample with reagents that are dispensed onto one or more surfaces of the lysing channel structures as described in more detail below. As depicted in FIG. 8A, the multiple lysing channel structures 142-142d and 144a-144b have an "F" shape on alternate layers of the multiple layers 12 and 13 that, when coupled to each other, enables the passage of a sample fluid through the fluidic circuit including the lysing channel structures 142-142d and 144a-144b.

In some implementations, the fluidic circuit formed by the layers 12 and 13 may be used to measure platelet counts in a sample of whole blood (or whole blood components). In such implementations, the lysing channel structures 142a-142d may be used to lyse red blood cells in whole blood, as described above, in order to improve the accuracy of performing a platelet count. For example, red blood cells lysing techniques may be used to reduce the likelihood that red blood cells in a fluid sample being mistakenly counted as platelets.

These example lysing channel structures 142-142d and 144a-144b may be cut from a layer of polymer material using, for example, a carbon dioxide laser. The structures are formed in at least two different layers that are laminated together to form a test cartridge. Lysing reagent may be loaded in the structures 142-142d and 144a-144b as dried. A fluid sample can be loaded into the cartridge and pulled into an area of known measurement at a known rate. In one particular implementation, an optical density measurement is then taken at wavelengths of around 506 nm and 880 nm. The wavelengths of measurement and types of measurement may vary in other implementations.

The example cartridge depicted (in part) in FIG. 8A may include an input opening where sample enters the cartridge and held in a sample well. The same is moved into optional channels that may serve to ensure that air bubbles are removed from the sample as it progresses through the fluidic circuit. The channels may be serpentine to provide a designed length and couples to the lysing structures 142-142d and 144a-144b on separate layers illustrated in FIG. 8A. These example lysing structures of each layer are fluidically coupled to optional channels and to the different lysing channel structures 142-142d and 144a-144b illustrated in the figure.

These example lysing channel structures 142-142d and 144a-144b can include a substantially straight backbone channel having a base portion and a top portion with two substantially equal lengths that are substantially parallel side channels extending substantially orthogonal to the top portion of the backbone channel (see description below regarding FIGS. 8B-C). Individual lysing channel structures 142-142d and 144a-144b that are coupled together as depicted in FIG. 8A may be arranged with side channels extending oppositely from the backbone, and coupled to the lower portion of the backbone of the lysing channel structure that first receives the sample. The channel structures 142-142d and 144a-144b can be arranged so that a channel structure receives the sample at ends of both side channels distal from its backbone. Additional fluid structures are also similarly coupled to form multiple lysing channel structures on alternate layers to pass the sample in sequence between the lysing channel structures.

Although FIG. 8A illustrates four lysing structures 142-142d and 144a-144b, in other implementations, as few as two, three, and more than four lysing channel structures may also be used. For example, a greater number of lysing channel structure may be used to provide chaotic diffusing of the sample with the reagent, which may be a dried reagent as described below.

Figures 8B, 8C:
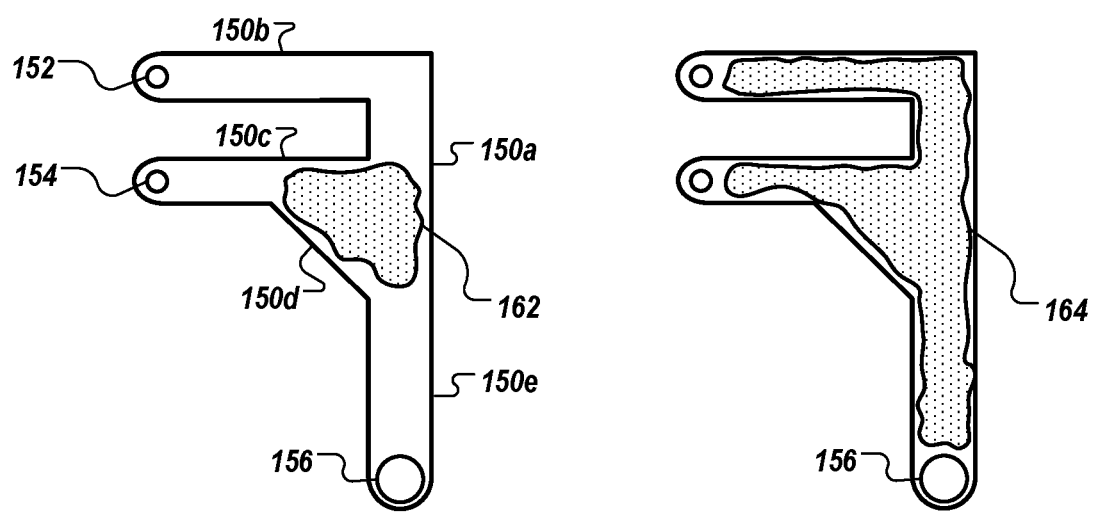
FIGS. 8B-8C illustrates top views of fluid structures with soluble substance coatings to aid in lysing red blood cells.

FIGS. 8B-C illustrate a top view of an example lysing channel structures with soluble substance coatings 158 and 160 applied to portions of the example structures to aid in lysing red blood cells, for example. The example lysing channel structure depicted in FIG. 8B includes a substantially straight backbone portion 150a with side channels 150b and 150c extending from the backbone portion forming an example structure that is referred to as an "F" shaped structure. The lysing channel structure can contain a triangular area defined by a diagonal sidewall 150d between a bottom wall of side channel 150c and a sidewall of the backbone 150a closest to a base portion 150e. The triangular area defined, in part, by the diagonal sidewall 150d is adapted to reduce bubble formation as the sample fluid moves through the channel structures. In some implementations, the diagonal sidewall 150d (and/or other walls or portions of the F channel) may be curved, and/or the triangular area defined by the diagonal sidewall 150d can have other shapes (including irregular shapes). Side channel 150b may also include such a triangular area defined, in part, by a diagonal sidewall similar to the diagonal sidewall 150d, in some implementations. In some implementations, the diagonal sidewall 150d and the triangular area it defines are optional and may not be included.

In operation, a fluid sample can enter the lysing channel structure through an inlet port 156 and can be split between side channels 150c and 150d. The portion of the sample within side channel 150b exits the lysing channel structure through an outlet port 152 and the portion of the sample within side channel 150c exits the lysing channel structure through the outlet port 154. The portions of the fluid exiting through each of the outlet ports 152 and 154 can then be recombined in a single channel in either a successive lysing channel structure, or another fluidic channel configured to match the present lysing channel structure. The splitting and recombining of the fluid sample can be repeated for each successive lysing structure. For example, the backbone of an upstream lysing channel structure can be coupled to the distal ends of one or more succeeding lysing channel structures. Lysing channel structures across different layers can be used, for example, to facilitate chaotic diffusing into the fluid sample.

The "F" shape of the lysing channel structures depicted in FIGS. 8A-C can allow for the separation and recombination of a sample fluid repeatedly over a lysing reagent, such as the soluble substance coatings 158 and 160, such that each cell is exposed to the reagent and the fluid sample is fully diffused, for example, at a point of measurement. The channels may be coupled, for example, to form a chaotic advection micromixer to assist in cell lysis. The cells may be red blood cells or other cells in other implementations, and may also work on bacteria.

In some implementations, the channel structures depicted in FIGS. 8A-C may be on the order of about 1 mm in width, resulting in total sample sizes of about 5-8 µl to sufficiently lyse the sample and fill a test chamber prior to analysis. The sizes of the channel may be varied in other implementations to optimize performance in view of the amount of sample generally available.

The surface of the lysing channel structures depicted in FIGS. 8A-C may be deposited with reagents including soluble substances to establish surface coatings (e.g., surface coatings 158 and 160) that can, for example, improve the lysing of red blood cells in order to release hemoglobin into the sample. Reagents and soluble substances deposited onto surfaces can be the same as, similar to, or different from those described above with regard to FIGS. 7A-C. For example, in some implementations, reagents that are applied to one or more surfaces of the lysing channels depicted in FIGS. 8A-C can include sodium deoxycholate and CHAPS within a carrier fluid that is a mixture of water and methanol. The concentrations and/or amounts of one or more soluble substances deposited onto the surfaces of the lysing channels can be optimized for lysing red blood cells, for example, based on the rate at which the sample diffuses into the lysing reagent. In one particular implementation, the reagent can include two percent weight by volume sodium deoxycholate and one percent weight by volume CHAPS in a mixture of water and methanol. The water in the carrier fluid can be used to prevent precipitation of the lysing reagent in the dispensing container. Other mixtures and proportions are also possible.

As described above with respect to FIGS. 7A-7C, the reagent dispensed onto a surface of the lysing channel structures depicted in FIGS. 8A-C may be evaporated to leave a soluble surface coating (e.g., coatings 158 and 160) onto one or more surfaces of the example lysing channel structures. The areas and locations at which the soluble surface coatings are applied can be varied, for example, based on different dispensing techniques used for testing applications. For instance, FIG. 8B depicts an implementation in which a soluble surface coating 158 is applied to a face (interior surface) of the triangle area that is defined in part by the diagonal sidewall 150*d*. Alternatively, FIG. 8C depicts another implementation in which a soluble surface coating 160 is applied on substantially the entire face (interior surface) of the lysing channel structure. In some implementations, the area of the soluble surface coating may be selected based on the volume of fluid sample to be analyzed within the lysing channel structures depicted in FIGS. 8A-C. Although FIGS. 8B-C depict the example lysing channel structures in a top down view, the lysing channel structures are three dimensional structures that define a volume in which lysing and interaction with the surface coatings by sample fluids can take place. The lysing channel structures depicted in FIGS. 8B-C can include the depicted face (surface), sidewalls that extend outward from the depicted face along the perimeter of the face, and another face that has the same general shape as the depicted face. The other face may or may not include ports 152-156. The surface coatings 158 and/or 160 may additionally or alternatively be applied to the other face of the lysing channel structures. Surface coatings may additionally and/or alternatively be applied to one or more portions of the sidewalls of the lysing channel structures.

After passing through the sequence of lysing channel structures depicted in FIGS. 8A-C, the exiting sample can include lysed cells of interests. The sample with the lysed cells may then be analyzed using various imaging techniques. In some implementations, the fluid sample can be whole blood (or whole blood components) and the cells that are lysed within the sequence of structures are red blood cells, which then release hemoglobin into the sample. The lysed sample may then be collected to take colorimetric readings at or around 506 nm and 880 nm to determine the concentration of hemoglobin.

The techniques described above with respect to FIGS. 8A-8C can be used to provide any of a variety of advantages, such as to more quickly lyse red blood cells compared to a straight or curved channel that does not include the lysing channel structures. For instance, the soluble surface coating (e.g., coatings 158 and/or 160) can be used to diffuse into whole blood or whole blood components to improve lysing speed. In addition, in some instances, the soluble substance coating (e.g., coatings 158 and/or 160) may also include additives that present and/or slows the lysis of white blood cells that are not of interest for analysis. This technique can be used to prevent the release of other cellular components that may potentially clog the outlet ports of the lysing channel structures depicted in FIGS. 8A-C.

In some implementations, a cartridge may include multiple fluidic circuits that each include sequences of lysing channel structures (as depicted in FIGS. 8A-C) for lysing specific cell types. For example, the surfaces of each sequence of lysing channel structures may be deposited with a different lysing reagent in order to perform a variety of colorimetric assays with a single sample volume. In one particular implementation, the cartridge may include a fluidic component that is capable of extracting plasma from a whole blood sample without the use of a centrifuge. The volume of extracted plasma may then be inserted into different lysing channel structures to analyze various cellular components within the plasma using colorimetric techniques.

Figure 9:
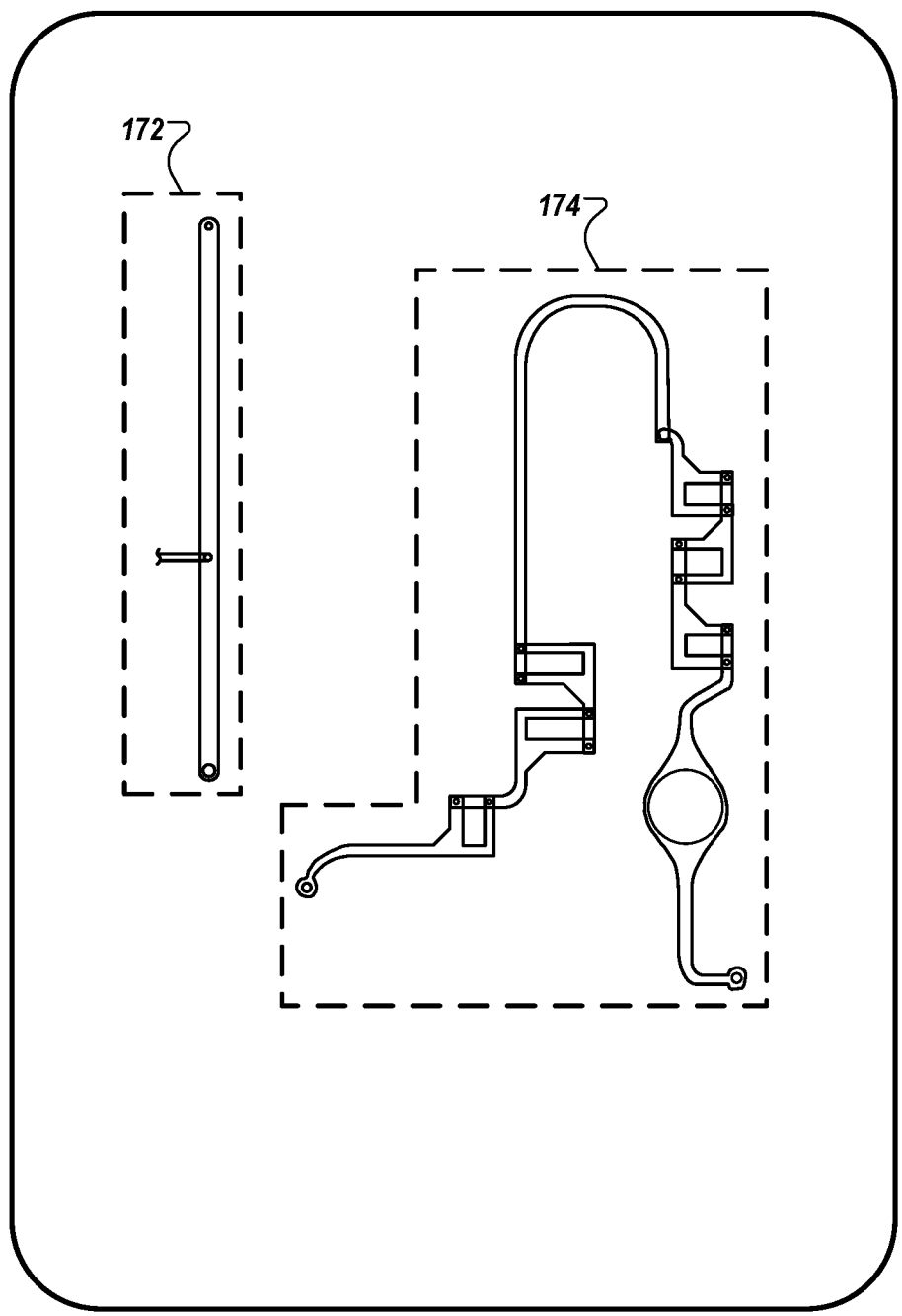
FIG. 9 illustrates a top view of a cartridge with multiple components and for performing different assays for a single fluid sample.

FIG. 9 illustrates a top view of a cartridge with multiple components 172 and 174 for performing different assays for a single fluid sample. The components 172 and 174 may represent separate channels of a fluidic circuit that is included within the cartridge 10. For instance, component 172 includes structures illustrated in FIGS. 7A-7C, and the component 174 includes structures illustrated in FIGS. 8A-8C. As described above, in implementations where the cartridge is used to analyze whole blood, the component 172 can be used to dispense a homogenous sample of whole blood and/or to determine a number of eosinophils in a volume of whole blood, and the component 174 can be used to determine hemoglobin concentration in the volume of whole blood. In this regard, a single cartridge can be used to perform multiple assays using one whole blood sample. The component 172 and the component 174 can be connected by one or more other circuits, either in series or from a common fluid source. For example, the component 172 can receive and dispense a homogenous blood sample (diffused with one or more soluble substances deposited onto the surfaces of the component 172). The blood sample dispensed from the component 172 can flow through one or more other circuits and into the component 174, at which point the fluid sample can diffuse one or more substances coating surfaces of the component 174. As described above with regard to FIGS. 8A-C, the component 174 includes two groups 176a-b of lysing channel structures that are connected in series, and each of these lysing channel structures within the groups 176a-b can be the same or different surface coatings (e.g., surface coatings 158 and/or 160).

The arrangement of the components 172 and 174 on the cartridge can be used, for example, to prevent reagents for each assay from interfering with one another. For instance, the cartridge may include a sample introduction chamber that diverts an injected volume of a sample fluid into two different fluid channels so that soluble substance coatings in each respective chamber do not interfere with the reactions between the soluble substance and the fluid sample in each channel.

Figure 10:
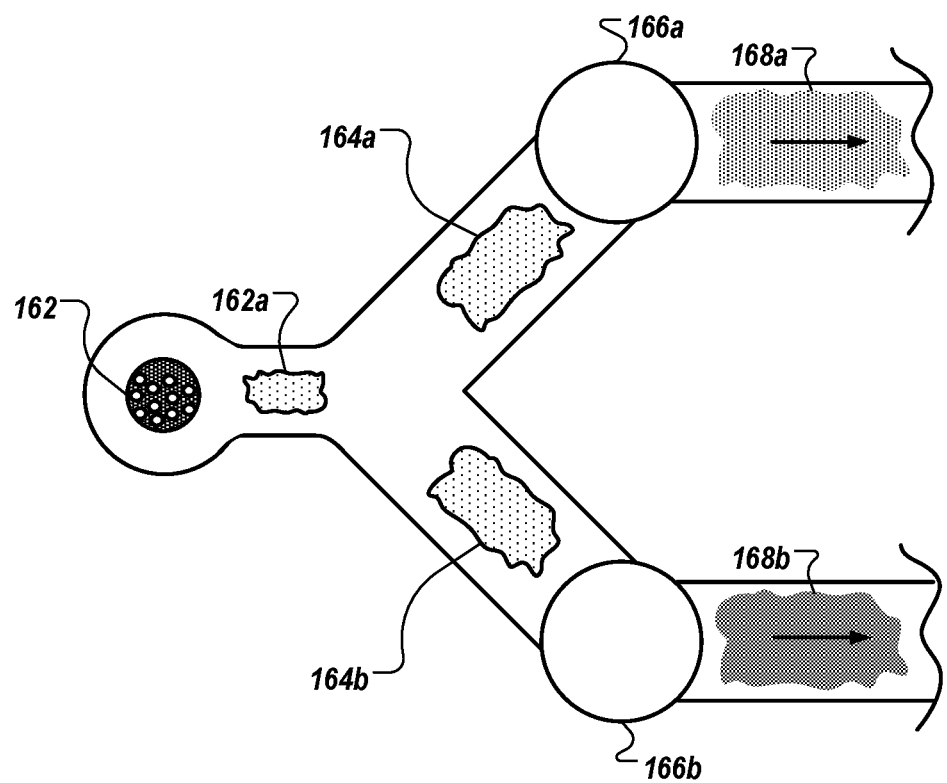
FIG. 10 illustrates a conceptual diagram of a sample loading port with multiple introduction channels with alternate anti-coagulants.

FIG. 10 illustrates an example of a sample introduction chamber that includes two diverging channels that separate volumes of a whole blood sample 162. The chamber may include a soluble substance coating 162a upstream of the two diverging channels, and different soluble substance coatings 164a and 164b deposited in each channel. In some implementations, the soluble substance coating 162a may be diffused into the entire volume of the whole blood sample 162 prior to separating different portions of the sample 162 into sample chambers 166a and 166b. For example, the soluble substance coating 162a may be an anticoagulant that is used to prevent coagulation of a finger-prick blood sample that is introduced into the chamber. Such a configuration with the substance coating 162a can be advantageous in that it can permit blood directly from a patient's body, such as from a finger prick, to be used as a sample without first having to be diffused with anticoagulant in a separate container, such as a vacuum sealed vial containing an anticoagulant substance.

The soluble substance coatings 164a and 164b can be deposited so that the portions of the sample 162 that are moved to sample chambers 166a and 166b include different mixtures of the sample 162 and the corresponding soluble substances. In one particular implementation, the soluble surface coating 164a may be a dried reagent of neutral red dye, whereas the soluble surface coating 164b may be a dried reagent that includes a mixture of sodium deoxycholate and CHAPS. In this implementation, the fluid portion 168a may be used to perform eosinophil counts as discussed previously with respect to FIGS. 7A-7C, and the fluid portion 168b may be used to perform hemoglobin counts as discussed previously with respect to FIGS. 8A-8C. A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A method comprising:
  depositing a first liquid with a first soluble substance coating onto a portion of one or more surfaces of a chamber of a fluidic circuit comprising:
    (i) chamber having one or more surfaces that define a volume to receive a fluid containing particulate matter, wherein the chamber includes, at least, a top region, a middle region, and a bottom region that, after at least a threshold time period has elapsed since the fluid is received into the chamber, contain different concentrations of the particulate matter, and
    (ii) an outlet port located at a position in the chamber that corresponds to the middle region;
  injecting a fluid containing particulate matter into the fluidic circuit; diffusing a portion of the first soluble substance deposited onto the portion of one or more surfaces of the chamber into at least a portion of the injected fluid containing particulate matter;
  after injecting the fluid containing particulate matter, waiting the at least threshold time period;
  dispensing a portion of the fluid containing particulate matter from the middle region of the chamber via the outlet port such that (i) the fluid containing particulate matter flows from the chamber and into the outlet port in a direction that is perpendicular to gravity, and (ii) the portion of the fluid containing particulate matter dispensed via the outlet port includes at least a portion of the diffused first soluble substance.

2. The method of claim 1, wherein:
  the first soluble substance coating comprises a fluorescent dye, and
  at least a portion of the particulate matter dispensed from the outlet port is tagged with the fluorescent dye.

3. The method of claim 2, wherein:
  the fluid containing particulate matter is whole blood,
  the fluorescent dye comprises a Neutral red dye, and
  a concentration of the Neutral red dye within the first soluble substance coating is sufficient to fluorescently tag eosinophils within the portion of the whole blood that is dispensed from the outlet port.

4. The method of claim 1, wherein the first soluble substance coating comprises a hydrophilic coating.

5. The method of claim 1, wherein the first soluble substance coating comprises a sample modifier that reacts with the particulate matter.

6. The method of claim 5, wherein the sample modifier comprises an antibody.

7. The method of claim 1, wherein the first soluble substance coating comprises a dried reagent and a carrier fluid, wherein the carrier fluid evaporates from at least a portion of the one or more surfaces of the chamber before the fluid containing particulate matter is received into the chamber.

8. The method of claim 1, wherein the first soluble substance coating is on an entirety of each of the one or more surfaces.

9. The method of claim 1, wherein the one or more surfaces comprises three surfaces that do not include the outlet port and the first soluble substance coating is on portions of each of the three surfaces.

10. The method of claim 9, wherein the portions of the three of the surfaces are in the middle region, which contains a concentration of particulate matter between a first threshold concentration of the particulate matter and a second threshold concentration of the particulate matter.

11. The method of claim 1, wherein the fluidic circuit further comprises:
  multiple lysing channel structures coupled to each other to pass the injected fluid containing particulate matter in sequence between the multiple lysing channel structures;
  a second soluble substance coating on at least a portion of surfaces of the multiple lysing channel structures that, after the injected fluid is received into the multiple lysing channel structures, diffuses into a portion of the injected fluid received into the multiple lysing channel structures; and a test chamber configured to receive the injected fluid containing particulate matter from the multiple lysing channel structures.

12. The method of claim 11, wherein the first soluble substance coating and the second soluble substance coating each comprise different soluble substances.

13. The method of claim 11, wherein the fluid containing particulate matter that is received into the chamber and the fluid containing particulate matter that is received into the multiple lysing channel structures are different portions of a same fluid sample.

14. The method of claim 11, wherein:
fluid containing particulate matter is whole blood, and
the second soluble substance coating comprises sodium deoxycholate and at least one additive that, after the second soluble substance diffuses into the portion of the whole blood received into the multiple lysing channel structures, prevents an increase in viscosity of the portion of whole blood received into the multiple lysing channel structures.

15. The method of claim 11, wherein each of the multiple lysing channel structures comprises:
a straight backbone channel having a base portion; and
a top portion with two equal lengths, parallel side channels extending orthogonal to the top portion of the backbone channel.

16. The method of claim 15, wherein the multiple lysing channel structures are arranged such that:
a first lysing channel structure receives the fluid containing particulate matter at its respective base portion, and
a second lysing channel structure has an end of at its respective base portion coupled to receive the fluid containing particulate matter from the top portion of the backbone of the first lysing channel structure.

* * * * *